(12) United States Patent
Agar et al.

(10) Patent No.: US 10,032,615 B2
(45) Date of Patent: Jul. 24, 2018

(54) SYSTEMS AND METHODS FOR SINGLE CELL CULTURE AND ANALYSIS BY MICROSCOPY AND MALDI MASS SPECTROMETRY

(71) Applicants: The Brigham and Women's Hospital, Boston, MA (US); Massachusetts Institute of Technology, Boston, MA (US)

(72) Inventors: Nathalie Y. R. Agar, Newton, MA (US); J. Christopher Love, Cambridge, MA (US); Denis Loginov, Cambridge, MA (US)

(73) Assignees: The Brigham and Women's Hospital, Boston, MA (US); Massachusetts Institute of Technology, Cambridge, MA (US)

( * ) Notice: Subject to any disclaimer, the term of this patent is extended or adjusted under 35 U.S.C. 154(b) by 13 days.

(21) Appl. No.: 14/741,257

(22) Filed: Jun. 16, 2015

(65) Prior Publication Data
US 2015/0364307 A1 Dec. 17, 2015

Related U.S. Application Data

(60) Provisional application No. 62/012,728, filed on Jun. 16, 2014.

(51) Int. Cl.
*H01J 49/04* (2006.01)
*G01N 21/64* (2006.01)

(52) U.S. Cl.
CPC ........ *H01J 49/0418* (2013.01); *G01N 21/648* (2013.01)

(58) Field of Classification Search
None
See application file for complete search history.

(56) References Cited

U.S. PATENT DOCUMENTS

| | | | | |
|---|---|---|---|---|
| 8,821,816 | B2 * | 9/2014 | Little | B01J 19/0046 422/501 |
| 8,865,479 | B2 * | 10/2014 | Love | B01L 3/50853 435/287.2 |
| 2009/0197295 | A1 * | 8/2009 | Fournier | H01J 49/0004 435/29 |
| 2009/0325262 | A1 * | 12/2009 | Hodneland | B82Y 30/00 435/176 |
| 2011/0117634 | A1 * | 5/2011 | Halamish | C12M 23/12 435/283.1 |
| 2016/0047799 | A1 * | 2/2016 | D'Aloia | G01N 33/6851 436/71 |
| 2016/0314583 | A1 * | 10/2016 | Couch | G01N 33/574 |

* cited by examiner

*Primary Examiner* — Shawn Decenzo
(74) *Attorney, Agent, or Firm* — Quarles & Brady LLP

(57) ABSTRACT

Systems and methods for single cell culture and analysis by microscopy and matrix assisted laser desorption ionization mass spectrometry are disclosed. The systems and methods isolate a plurality of cells in a plurality of wells such that a predetermined number of the plurality of wells contain one and only one cell. The plurality of wells allow for optical interrogation of the cells and subsequent matrix assisted laser desorption ionizing of molecules within the cells.

20 Claims, 23 Drawing Sheets
(18 of 23 Drawing Sheet(s) Filed in Color)

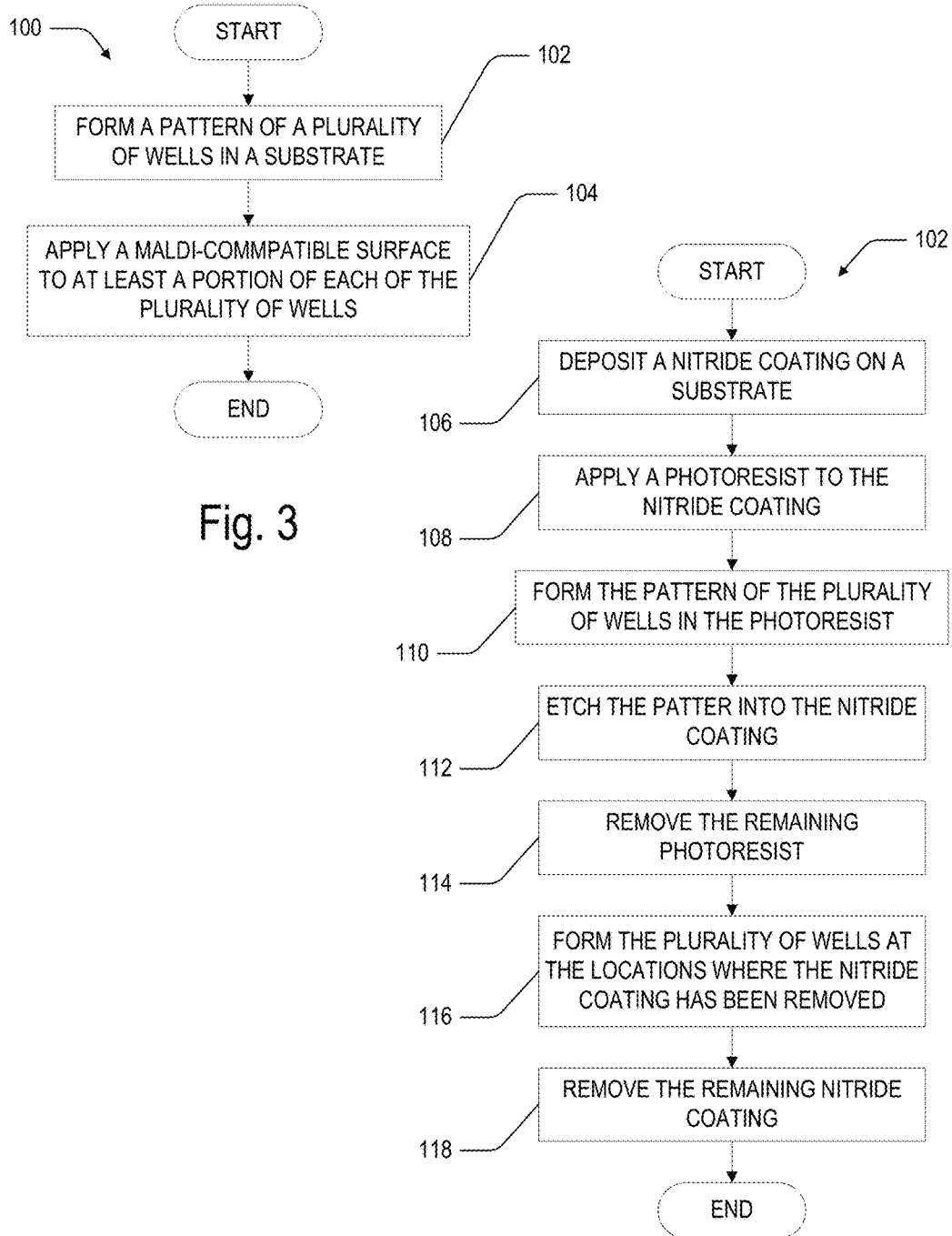

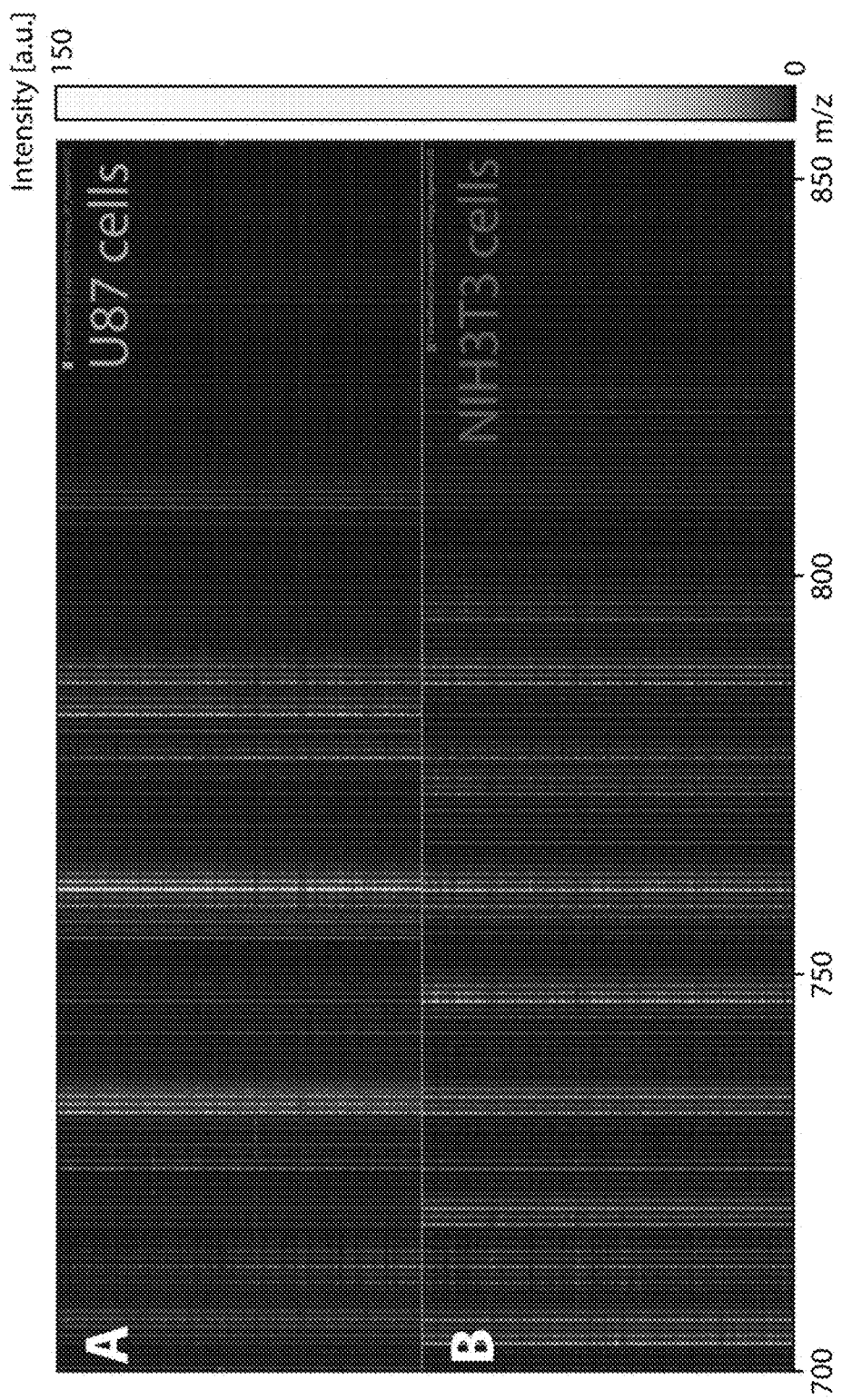
Fig. 16 A&B

Fig. 22 A&B

SYSTEMS AND METHODS FOR SINGLE CELL CULTURE AND ANALYSIS BY MICROSCOPY AND MALDI MASS SPECTROMETRY

CROSS-REFERENCE TO RELATED APPLICATIONS

This application claims priority to U.S. Provisional Patent Application No. 62/012,728, filed Jun. 16, 2014, the entire contents of which are incorporated herein by reference.

GOVERNMENT SUPPORT

This invention was made with government support under W911NF-13-D-0001 awarded by the Army Research Office and OD007383 awarded by the National Institutes of Health. The government has certain rights in the invention.

BACKGROUND

This disclosure relates generally to single cell culture and analysis by microscopy and MALDI mass spectrometry.

The last several decades have seen a tremendous progress in the understanding of biological processes. An ever-growing number of assays, made available through highly-automated tools such as quantitative PCR instruments and high-throughput DNA sequencers, have allowed the analysis of molecular mechanisms of these processes in exquisite detail.

Despite these advances, research in many important fields, such as immunology and cancer biology, has made it increasingly clear that bulk measurements (i.e. on the level of cell populations and tissue homogenates) can mask characteristics of individual cells or subsets of cells that contribute significantly to biological processes, but may not be identical to the "population average" measured by these techniques. Such heterogeneity appears not only in genetically diverse populations (as in the case of many tumors, or T and B lymphocytes), but also at the clonal level, based on differences in epigenetic states of the cells and stochasticity in cellular signaling. In addition, interactions between individual players may not be resolved if only an "average" behavior is studied. As a result, traditional methods may draw a misleading picture of dynamic responses of cells to the given perturbations, necessitating development of technologies for single-cell analysis.

Important classes of measurements include characterization of genotype, proliferation, cell surface markers, secreted molecules and interactions between individual cells. Tracing these parameters for every cell may reveal not only new biology (such as specific pathways and interactions in the immune system), but also inform diagnosis and treatment (for example, based on known mutations in cancer). Although taking in vivo measurements would in many cases be preferable to preserve the natural state of cells and their microenvironments, it is often impossible or impractical. In vitro measurements are less restrictive, but may also pose limitations on the number and types of assays that may be applied. First, they should offer a means to isolate individual cells for subsequent interrogation. They should also be sensitive enough to reliably detect signals associated with each cell. The number of simultaneously detected signals (multiplexity) may become another limitation. Some measurements (such as genetic profiling) may be done as an end-point assay, while others (such as functional or phenotypic characteristics) may be repetitive due to their non-destructive nature. Another important aspect is the throughput of any assay, which poses a practical limit on how many measurements and on how many cells can be feasibly done in a given time; methods that process cells in parallel may be much more efficient than serial ones. No less important is the number of cells required for a particular method, which implies the kinds of samples that could be processed with it: while cell lines and animal models are an abundant source of material used in research, clinical samples often barely meet this criterion. In this regard, any method that preserves viability and identity of cells for subsequent analyses (i.e. being modular) may provide additional flexibility. Finally, fine control over individual cells and their measurements should be carefully balanced with the overall simplicity of the approach, as doing so may drastically affect the costs and labor spent on any analysis.

Optical tools have become a de-facto standard for the majority of measurements in biological research, both at the bulk and the single-cell levels. Indeed, high sensitivity and resolution (down to the single-molecule level) enabled by advanced light sources and detectors—lasers, photomultiplier tubes (PMTs), electron multiplying charge-coupled devices (EMCCDs) etc. (which in turn, resulted from advances in physical sciences and microfabrication)—coupled with the generally non-destructive nature of optical measurements (allowing repeated, time-course and modular experiments) and an ever-growing availability of fluorescent probes, provided a unique framework for studying biological processes not easily achieved with any other physical observations. However, optical measurements still suffer from reduced multiplexity due to the overlapping spectra of the dyes, the requirement for labels specific to target molecules, and oftentimes a necessity to amplify the analytes (such as nucleic acids). As such, a number of orthogonal methods that complement or substitute fluorescence measurements by relying on alternative physics, have been developed: Raman spectroscopy, mass spectrometry, methods using electric and magnetic fields (capillary electrophoresis (CE), dielectrophoresis (DEP), iso-dielectric separation (IDS)), as well as mechanical forces (acoustic or inertial focusing). All these techniques greatly expand the arsenal of tools available for single-cell analysis, allowing researchers to choose the best set of tools for each case.

While the majority of tools for bulk and even single-cell analysis has traditionally been developed at the "macro" scale, the advancement of technologies for fabrication of microstructures in recent years has enabled production of miniaturized systems, or "lab on a chip" (LoC) devices. These tools utilize the concept of confinement of cells or their lysates and associated reagents to a small volume, often on the order of nanoliters or less. They not only serve to isolate cells from each other, but also increase local concentrations of analytes to achieve higher sensitivity, reduce cost of consumables and time spent on each analysis (often by processing many cells or reactions in parallel or in fast iterations), as well as automate analytical pipelines and reduce potential for human error. Prominent examples include passive and actively actuated microfluidic traps, droplet encapsulation and microwell arrays. Passive devices trap one or a few cells in their structures and trace their growth or responses to stimuli with fluorescence microscopy; although efficient trapping is possible, it provides inhomogeneous shared environment dependent on the position of a cell in the stream. Actively actuated traps may offer better control over microenvironment and cross-contamination, but require the use of a complicated set of microfluidic valves and pumps that is limited by the number of connections and as such is not scalable to large numbers of cells (>10³-10⁴). Droplet-based devices encapsulate cells in small volumes of water-in-oil emulsions and provide room for combinatorial screening and sorting; although highly-controlled and efficient loading is possible, and cell viability may be preserved over extended time, controlling individual droplets still requires significant manipulations. In all cases above, a high degree of control, efficiency and throughput, guided by computational optimization based on hydrodynamics simulations, is achievable; however, it comes at a cost of an overall complexity of the analysis and limited potential for retrieval of individual cells of interest.

The most common choice of material for LoC devices has been poly(dimethylsiloxane) (PDMS). Its wide adoption in academic labs is based on a unique combination of properties: ease of replication based on soft lithography, high optical transparency and low autofluorescence compared to common plastics, versatility in surface modifications and elasticity allowing it to conformally seal against hard surfaces and be actuated, permeability to gases, relative inertness and biocompatibility, along with a few others. Even with all these advantages, however, PDMS is not an ideal material for some applications: its high permeability to small non-polar molecules and water vapor may severely affect measurements involving hydrophobic moieties and affect viability of cells sensitive to changes of osmolality in the media; its high elasticity precludes fabrication of microstructures with aspect ratios higher than 2:1 (e.g. tall posts) or lower than 0.2 (shallow channels or wells), and affects reliable registration for large-scale devices. Finally, and perhaps most importantly, PDMS is not readily amenable to large-scale replication: while manual handling in an academic lab is straightforward, it takes a substantial time to cure the polymer (1-2 h), and the overall process may leave residues on the mold. Industrial processes (such as injection molding), to the contrary, benefit from materials that can easily be processed and ejected in a matter of seconds, making large-scale production cost effective.

The World Health Organization (WHO) classifies over 125 types of brain tumors based on histopathological evaluation, assigning type, subtype and grade (I-IV) to each one of them. Gliomas, tumors of the tissue that support and protect neurons, account for 30% of them, with astrocytoma and oligodendroglioma being the most malignant forms, 70% grade III or higher. Glioblastoma (GBM) is astrocytoma grade IV, with a median survival of 12 to 15 months. Meningiomas account for another 34.7% of all brain tumors. GBM is infamous for being one of the most heterogeneous tumors in existence, as defined by numerous phenotypic and genetic factors. Tumor sustainability and drug resistance are direct results of this heterogeneity, wherein tumor survives due to hyper-adaptive subpopulations. Identification of these tumors based on histopathology and magnetic resonance imaging (MRI) can be challenging, and decisions on surgical resection are in many cases too aggressive if the boundary between the tumor and the normal tissue is unclear. This results in postoperative morbidity, i.e. undesired neurological deficits.

To help with identification and characterization of tumor heterogeneity, new modalities for tumor imaging are needed. More complete knowledge about the tumors could inform clinical decisions, including surgical decisions and optimization of adjuvant treatment, and further enhance our understanding of tumor biology. Whereas conventional tools for resolving heterogeneity revolve around fluorescence microscopy at the proteomic and genomic levels, mass spectrometric techniques for identification and quantification of complex (≥100 Da) molecules have also become available in the last two decades. Desorption electrospray ionization (DESI) mass spectrometry has recently been shown to accurately identify tumor type, grade and cellularity based on lipid imaging of tissue sections from stereotactic biopsies with a high degree of accuracy in near real time (i.e., during an operation). Matrix-assisted laser desorption/ionization (MALDI) mass spectrometry imaging (MSI) has been used for a proteomic-based prognosis in a similar context. These advances demonstrate a clear clinical impact associated with such technologies.

While conventional methods rely on expensive probes (such as antibodies and DNA tags) that are specific to the molecules of interest, mass-spectrometric techniques mentioned above allow for direct imaging of small and large molecules without the need for any labeling. In case of small molecules (such as lipids and metabolites), highly specific probes may not even exist. Additionally, this enables work in "discovery mode", where mass spectrum signals can be analyzed with little or no a priori knowledge of what particular molecules to look for, which would not be possible with methods that rely on labeling of target analytes. Little or no sample preparation also reduces the time and effort required for MSI compared to probe-based analyses.

Thus, a need exists for systems and methods that allow a user to culture and interrogate a population of cells on a cell-by-cell basis, using fluorescence microscopy and MALDI-MSI.

BRIEF SUMMARY OF THE INVENTION

The present invention overcomes the aforementioned drawbacks by providing systems and methods for single cell culture and analysis by microscopy and MALDI mass spectrometry.

In one aspect, this disclosure provides an isoalted cell analysis device. The device can include a substrate having a first surface including a plurality of wells. The first surface including the plurality of wells can be configured to receive a suspension including a plurality of cells. The plurality of wells can be configured to have at least 25% of the wells contain one and only one cell upon receiving the suspension including a plurality of cells, waiting a length of time to allow the plurality of cells to settle, and removing an excess of the suspension from the first surface. Each of the plurality of wells can be configured to allow an isolated cell contained within one of the plurality of wells to be optically interrogated and to subsequently have molecules of the isolated cell be ionized by matrix assisted laser desorption ionization via a laser impinging on the isolated cell at an angle between 5 and 85 degrees relative to the first surface.

In another aspect, this disclosure provides a method of making a single cell analysis device. The method can include forming a pattern of a plurality of wells in a substrate; and applying a MALDI-suitable material to at least a portion of each of the plurality of wells in the substrate.

In yet another aspects, this disclosure provides a method of optically interrogating and subsequently matrix assisted laser desorption ionizing a plurality of isoalted cells. The method can include one or more of the following steps: isolating a plurality of cells in a plurality of wells, such that at least 25% of the plurality of wells contain one and only one cell of the plurality of cells; optically interrogating at least the plurality of isolated cells located in the plurality of wells containing one and only one cell; introducing a matrix assisted laser desorption ionization matrix into the plurality of wells; and matrix assisted laser desorption ionizing the at least one cell.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

The patent or application file contains at least one drawing executed in color. Copies of this patent or patent application publication with color drawing(s) will be provided by the Office upon request and payment of the necessary fee.

FIG. 3 is a flowchart illustrating a method, according to one aspect of the present disclosure.

FIG. 4 is a flowchart illustrating a method, according to one aspect of the present disclosure.

FIG. 16 is a visualization of matrices of the phospholipid signal (700-860 Da, horizontally) across 1152 spectra (vertically) for each of U87 cells (A) and NIH3T3 cells (B), as described in Example 1.

Figure 1:
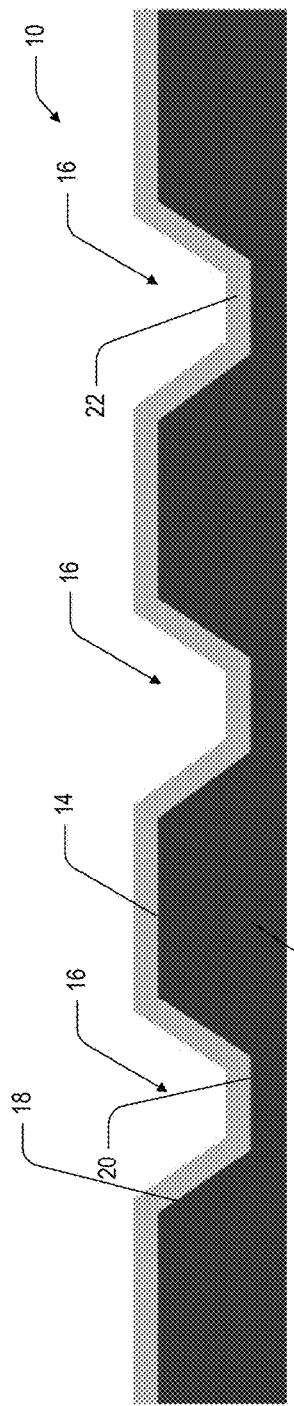
FIG. 1 is an illustration of a cross-section of a device, according to one aspect of the present disclosure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices, and methods relating to improved ultrasound treatment efficiency and operation are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10. Features described with respect to the systems can be utilized in the methods described herein, and features described with respect to the methods can be utilized in the systems described herein, unless context clearly dictates otherwise.

Devices of the Present Disclosure

Referring to FIG. 1, this disclosure provides a device 10. The device 10 can include a substrate 12 having a first surface 14 containing a plurality of wells 16. Each well can have at least one side wall 18 and at least one bottom surface 20.

The substrate can be silicon, PDMS, cyclic olefin polymer, polypropylene, poly(methyl methacrylate), polystyrene, conductive metals, such as gold, silver, platinum, or copper, indium tin oxide, III-V semiconductors, such as gallium arsenide, or a combination thereof.

The first surface 14 containing a plurality of wells 16 can be configured to receive a suspension comprising a plurality of cells.

The plurality of wells 16 can be configured to have at least 25%, at least 30%, at least 35%, at least 40%, at least 45%, at least 50%, at least 55%, at least 60%, at least 65%, at least 70%, or at least 75% of the wells 16 contain one and only one cell upon receiving the suspension comprising a plurality of cells, waiting length of time to allow the plurality of cells to settle, and removing an excess of the suspension from the first surface. It should be appreciated that the structural requirements of the device in order to achieve a probabilistic loading of one and only one cell into a certain percent of the wells is highly dependent on the characteristics of the cells, the concentration of the cells within a suspension that is applied to the device, and the methods used to apply the suspension to the device and isolate the cells in respective wells. As such, some structural features of the device relating to the probabilistic loading, such as the dimensions of the wells, cannot be defined in absolute terms. Rather, these structural features of the device are described in terms of the desired results, the general design principles are described herein, a specific, exemplary functioning device is described below in the examples, and a person having ordinary skill in the art would appreciate how to determine the structural features necessary to achieve the desired probabilistic loading.

Each of the plurality of wells can be configured to allow an isolated cell contained within one of the plurality of wells to be interrogated by optical spectroscopy and to subsequently have molecules of the isolated cell be ionized by matrix assisted laser desorption ionization via laser impinging on the isolated cell at an angle between 5° and 85° relative to the first surface, including but not limited to, an angle between 10° and 80°, between 15° and 75°, between 20° and 70°, between 25° and 65°, between 30° and 60°, or between 35° and 55° relative to the first surface.

Side walls 18 of the wells 16 can be flat, curved, or combinations thereof. In certain aspects, side walls 18 of the wells 16 can be vertical or can have an inward slope.

The bottom surface 20 of the wells 16 can be flat, curved, conical, or combinations thereof. In certain aspects, a well 16 can have more than one bottom surface 20, for example, in the case where the lowest point in a well 16 is an intersection between surfaces.

Each well can include at least one MALDI-compatible surface 22. In some aspects, the entire surface of the well can be a MALDI-compatible surface. In some aspects, a bottom surface of the well can be a MALDI-compatible surface. A MALDI-compatible surface can be an electrically conductive film, including but not limited to, indium tin oxide, conductive metals, such as gold, silver, platinum, or copper, silicon, III-V semiconductors, such as gallium arsenide, or combinations thereof.

In certain aspects, the device can be less than optically transparent. When the device is not optically transparent, it may be necessary to slope the side walls of the wells in order for an angled light source, such as the one typically used in MALDI, can illuminate the bottom of the wells (i.e., the place where the cell is most likely to reside). In certain aspects, the side walls of the well can be configured to not be perpendicular to the surface. In certain aspects, the bottom of the well is smaller than the top opening of the well. In certain aspects, the side walls of the well have an inward slope of between 10° and 80° relative to the surface, including but not limited to, an inward slope of between 15° and 75°, 20° and 70°, 25° and 65°, 30° and 60°, 35° and 55°, or an inward slope of between 40° and 50°.

In certain aspects, the device can be substantially optically transparent. In configurations where the device is substantially optically transparent, the side walls can be perpendicular to the surface or can have an inward slope of between 10° and 90° relative to the surface.

The wells 16 can have a depth of between 1 μm and 250 μm, including but not limited to, a depth between 2 μm and 100 μm, 3 μm and 90 μm, 5 μm and 80 μm, 10 μm and 75 μm, or a depth between 25 μm and 60 μm.

The wells 16 have an opening in the first surface 14 of the substrate 12 that can have a pre-determined geometric shape. In certain aspects, the opening can have a circular shape, a triangular shape, a square shape, or other similar geometric shapes. The wells 16 can have an opening having a diameter, defined as the longest physical dimension of the opening (i.e., the diameter of a circle, the length of an edge of a triangle, the length of a diagonal of a square, etc.) of between 10 μm and 100 μm, including but not limited to, a longest physical dimension of between 15 μm and 90 μm, 20 μm and 80 μm, 25 μm and 75 μm, or a longest physical dimension of between 40 μm and 60 μm. The wells can have an opening having an area of between 100 μm$^2$ and 10,000 μm$^2$, including but not limited to, an area of between 200 μm$^2$ and 5000 μm$^2$, 300 μm$^2$ and 2500 μm$^2$, or an area between 500 μm$^2$ and 1000 μm$^2$.

The wells 16 can have a volume of between 1 pL and 10 nL, including but not limited to, a volume of between 10 pL and 1 nL, or a volume between 50 pL and 100 pL.

The wells 16 can have a smallest nearest neighbor distance of between 5 μm and 100 μm, including but not limited to, a smallest nearest neighbor distance of between 10 μm and 90 μm, 15 μm and 75 μm, or a smallest nearest neighbor distance of between 25 μm and 60 μm.

In certain aspects, the device 10 can include one or more registration marks, which can serve as an identifier for the device 10, as well as an internal reference point for identifying locations on the device 10.

In certain aspects, the device 10 can include one or more calibration areas, which can include one or more features at a depth that is the same as the depth of the plurality of wells. By using the calibration areas, the device 10 can be used for MALDI-MSI and can account for the difference in distance between the first surface 12 and the bottom surface 20.

Figure 2:
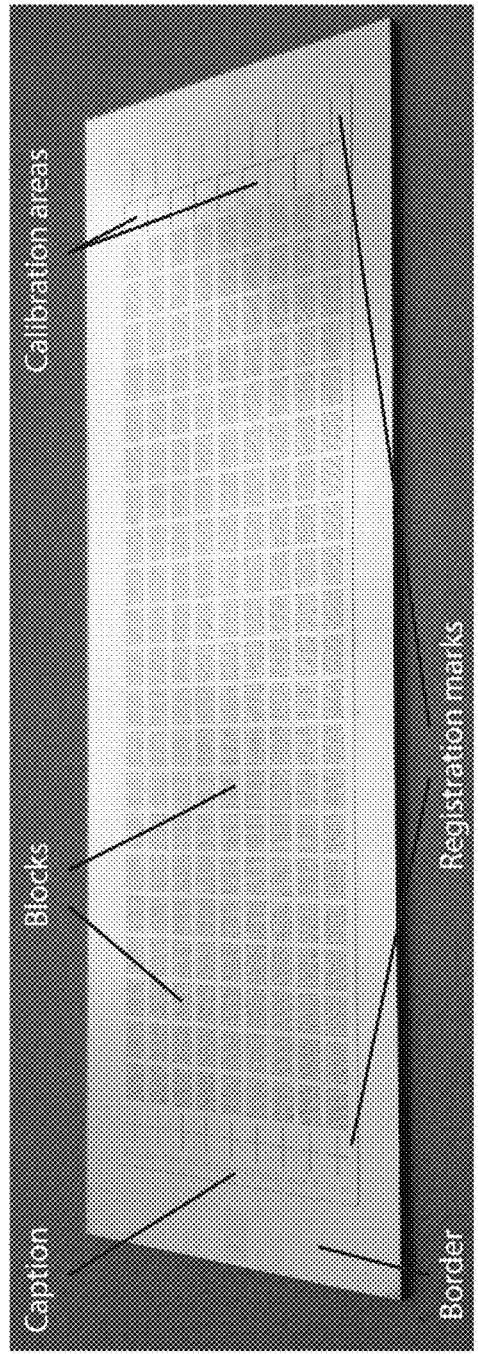
FIG. 2 is an image of the device as described in Example 1.

Referring to FIG. 2, an image of a device 10 prepared as set forth below in Example 1 is shown.

Methods of Making a Device of the Present Disclosure

Referring to FIG. 3, this disclosure provides a method 100 of making a device. At process block 102, the method 100 can include forming a pattern of a plurality of wells in a substrate. At process block 104, the method 100 can include applying a MALDI-compatible surface to at least a portion of each of the plurality of wells in the substrate.

Referring to FIG. 4, one aspect of a method 102 of forming a pattern of a plurality of wells is described. At process block 106, the method 102 can include depositing a nitride coating on a substrate. At process block 108, the method 102 can include applying a photoresist to the nitride coating on a first surface of the substrate. At process block 110, the method 102 can include forming the pattern of the plurality of wells in the photoresist, optionally by using UV light and a mask (a Cr mask in some aspects) having a negative of the pattern. At process block 112, the method 102 can include etching the pattern into the nitride coating, optionally by applying a plasma, optionally an $SF_6$ plasma, to the first surface. At process block 114, the method 102 can include removing the remaining photoresist, optionally by using a piranha solution. At process block 116, the method 102 can include forming the plurality of wells at the locations where the nitride coating has been removed, namely, the pattern, optionally using a KOH solution. At process block 118, the method 102 can include removing the remaining nitride coating, optionally by using an $H_3PO_4$ solution.

In other aspects, the method 102 of forming a pattern of a plurality of wells in a substrate can be accomplished by the methods described in U.S. Patent Application Pub. No. 2011/0124520, which is incorporated herein in its entirety by reference. In some aspects, the method 102 of forming a pattern of a plurality of wells in a substrate can include the methods described below in the METHODS section.

Methods of Performing Fluorescence Microscopy and MALDI on a Single Cell

Figure 5:
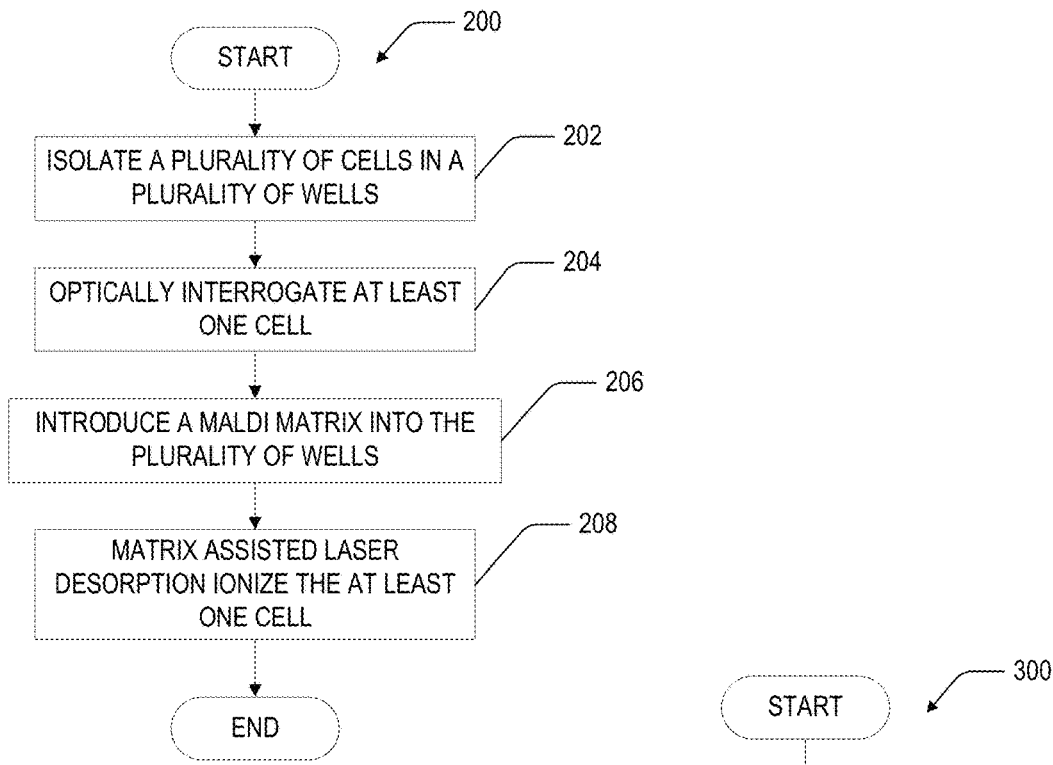
FIG. 5 is a flowchart illustrating a method, according to one aspect of the present disclosure.

Referring to FIG. 5, this disclosure provides a method 200 of optically interrogating and subsequently matrix assisted laser desorption ionizing molecules from a single cell. At process block 202, the method 200 can include isolating a plurality of cells in a plurality of wells, such that at least 50% of the plurality of wells contains one and only one cell of the plurality of cells. At process block 204, the method 200 can include optically interrogating at least one cell. At process block 206, the method 200 can include introducing a MALDI matrix into the plurality of wells. At process block 208, the method 200 can include matrix assisted laser desorption ionizing the at least one cell. In certain aspects, the method 200 can include fixing the plurality of cells in the plurality of wells.

Figure 6:
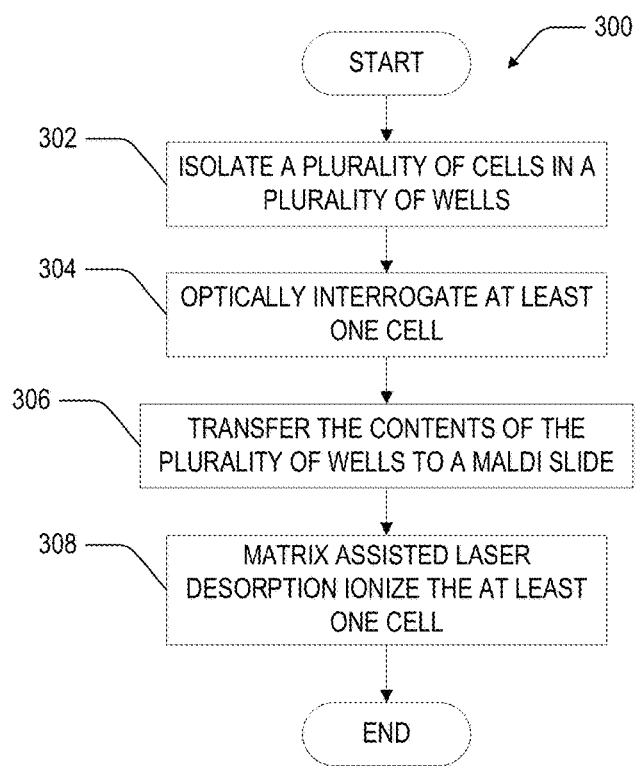
FIG. 6 is a flowchart illustrating a method, according to one aspect of the present disclosure.

Referring to FIG. 6, this disclosure provides a method 300 of optically interrogating and subsequently matrix assisted laser desorption ionizing a plurality of isolated cells. At process block 302, the method 300 can include isolating a plurality of cells in a plurality of wells, such that at least 50% of the plurality of wells contains one and only one cell of the plurality of cells. At process block 304, the method 300 can include optically interrogated at least one cell. At process block 306, the method 300 can include transferring the contents of the plurality of wells to a slide having a MALDI-compatible surface. At process block 308, the method 300 can include matrix assisted laser desorption ionizing the at least one cell.

In certain aspects, isolating a plurality of cells in a plurality of wells, such that at least 25% of the plurality of wells contain one and only one cell of the plurality of cells can include the following steps: contacting a first surface including the plurality of wells with a suspension comprising a plurality of cells; waiting a pre-determined period of time to allow the plurality of cells to settle into the plurality of wells; and removing excess suspension. The suspension can have a concentration of cells of between 1000 cells/mL and 500,000 cells/mL, including but not limited, a concentration of cells of between 10,000 cells/mL and 250,000 cells/mL, 20,000 cells/mL and 100,000 cells/mL, 25,000 cells/mL and 75,000 cells/mL, or a concentration of cells of between 40,000 cells/mL and 60,000 cells/mL.

In certain aspects, the optical interrogation can be fluorescence spectroscopy, fluorescence microscopy, Raman spectroscopy, Stimulated Raman Imaging, absorbance microscopy, surface plasmon resonance, infrared imaging, near-field imaging, combinations thereof, and the like.

In certain aspects, the methods 200, 300 can include registering a location of the plurality of cells within the plurality of wells using the results of the optical interrogation.

In certain aspects, the methods 200 can include accounting for reflections. Accounting for reflections can include locating an apex of a cross, formed by reflection locations, as described below in the METHODS section.

In certain aspects, the product of matrix assisted laser desorption ionizing can be introduced to a mass spectrometer for the purposes of mass spectrometry analysis or MSI.

In certain aspects, the methods 200, 300 can include generating a report including an analysis of the plurality of cells, including but not limited to, identifying the relative percentage of different cell populations, identifying the prevalence of certain cellular components in different cells, identifying the state or identity of cell populations, identifying stage of the cell cycle for a given cell population, and the like.

The methods 200, 300 described herein can also be used to investigate the effects of introducing certain defined perturbations, such as drug treatment to individual cells. In certain aspects, the method 200, 300 can include introducing one or more defined perturbations to isolated cells, waiting some time for the perturbation to effectuate, and then proceeding with the methods 200, 300 including MALDI.

Methods

Chip Design and Fabrication.

Mask Design.

Figure 7:
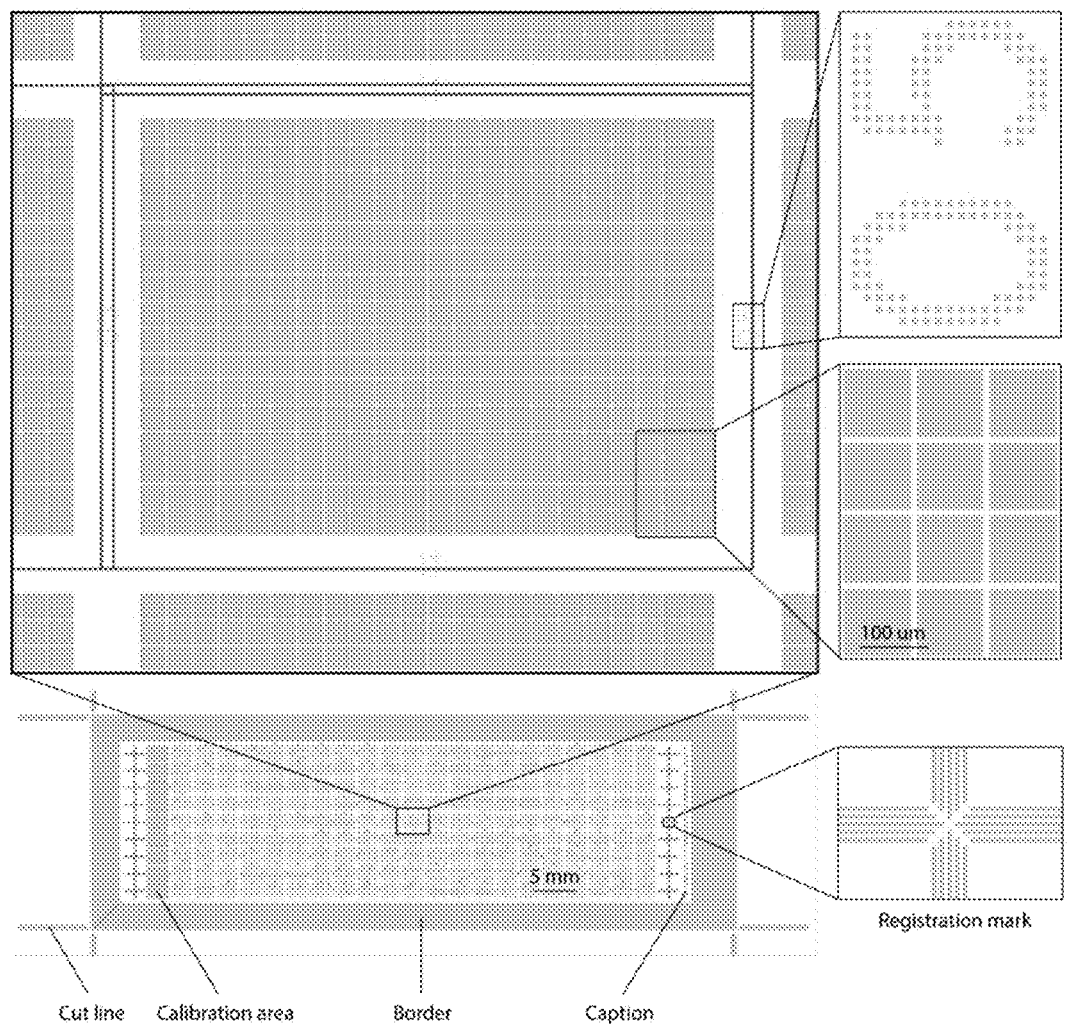
FIG. 7 is a mask for making a device, according to one aspect of the present disclosure.

A mask for a chip (device), as shown in FIG. 7, was designed using an in-house Perl script and an official DXF Reference specification for the open file format used by Autodesk AutoCAD. All features were "drawn" as non-intersecting closed polylines to meet the requirements for plotting set by the masking companies. The final file was converted from DXF to GDSII format and checked in Bay 47 Technology LinkCAD. The file was then sent for production to Photo Sciences Inc., Torrance, Calif.; the mask was made on a 7" soda-lime glass at CD 3 µm, with clear features, chrome side down.

Fabrication.

Figure 8:
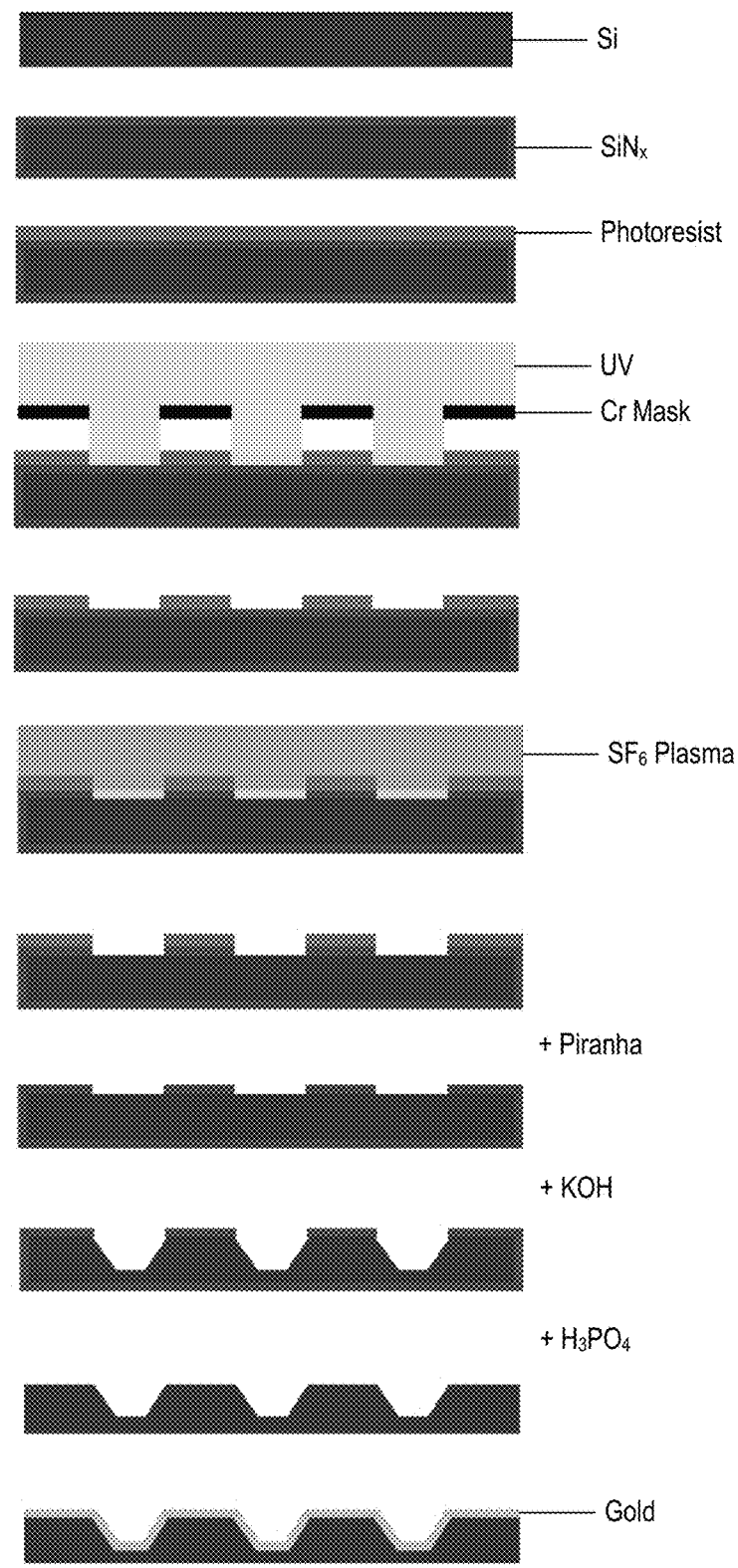
FIG. 8 is a schematic of a process of making a device, according to one aspect of the present disclosure.

The fabrication of the Si chip was carried out in class 10 (the Integrated Circuits Laboratory, ICL) and 100 (the Technology Research Laboratory, TRL) cleanroom facilities of the Microsystems Technology Laboratories (MTL) at MIT. The process is shown schematically in FIG. 8. 6"<100> Si wafers (prime grade, CZ, Ntype Phos., resistivity 4-7 Ω-cm, thickness 600-650 µm) were supplied by MTL from SunEdison, Maryland Heights, Mo. LPCVD silicon nitride was deposited by MTL staff in SVG/Thermco 7000

Series vertical thermal reactor (VTR). Photoresist processing was performed on automated SSI 150 coater/developer track ("coater6") using a standard recipe; briefly, wafers were treated with hexamethyldisilazane (HMDS, Sigma Aldrich, St. Louis, Mo.) and SPR700 v1.2 positive photoresist was spun-on for ~1 μm thickness and pre-baked at 95° C. The photoresist was exposed for 5 sec in Electronic Visions 620 mask aligner; no precision alignment was necessary, but the mask and the wafer flat were assured to not be askew relative to each other. The photoresist was then developed with in-line developer on coater6. The silicon nitride was dry-etched for a total of 120 sec with SF6 plasma in Lam Research Model 490B. The photoresist was stripped with piranha solution, a 1:3 mixture of 30% hydrogen peroxide ($H_2O_2$) to concentrated sulfuric acid ($H_2SO_4$) (acid first), for 10 min. Anisotropic wet etching of Si was performed with 20% wt. solution of potassium hydroxide (KOH) in water at 80° C. for ~50 min to achieve ~50 μm deep wells. The quality of etching was inspected in a reflected light microscope. Wafers were cleaned from KOH with a double-piranha protocol (10 min piranha, rinse in DI water, 10 min piranha, dump-rinse) as a requirement to use the next (CMOS-compatible) acid hood. The remaining silicon nitride was stripped with 85% wt. phosphoric acid at 165° C. for 20 min. Finally, Sloan 8 KV electron-beam evaporator was used to deposit 10 nm of Ti and 100 nm of Au. The wafers were then cut to individual chips using Disco Abrasive System Model DAD-2H/6T die saw.

The plastic chips (devices) were made by Edge Embossing LLC from a master with the use of two intermediate elastomeric molds. The master consists of SU-8 posts patterned on a 4" Si wafer using standard photolithography performed at the Institute of Electronics and Nanotechnology of Georgia Institute of Technology; the masks were ordered from Photo Sciences Inc. with dark features, chrome side down. ITO and Au were deposited on plastic chips in AJA Orion 5 sputtering system at class 10,000 (the Exploratory Materials Laboratory, EML) facility at MTL. Characterization of the chips with scanning electron microscopy was performed in secondary electron mode at low kilovoltage on general-purpose microscopes, either JEOL 5910 at the MIT Center for Materials Science and Engineering (CMSE) or JEOL 6010LA at the MIT Institute for Soldier Nanotechnologies (ISN).

Sample Preparation.

Cell Culture.

NIH3T3 (mouse fibroblast) engineered to express enhanced green fluorescent protein (eGFP) reporter gene or/and U87-MG (human primary glioblastoma) cells were cultured in Dulbecco's Modified Eagle's Medium (DMEM, Fisher Scientific, Pittsburgh, Pa.) with 10% fetal bovine serum (FBS), 1% Penicillin-Streptomycin and 1% L-glutamine (Life Technologies).

The U87-MG were stained with 50 μg/mL 4',6-diamidino-2-phenylindole (DAPI, Invitrogen, Grand Island, N.Y.) during 1 min and then washed 3 times in 1×PBS to remove excess dye prior to their incubation onto the chip.

Tissue Dissociation.

Research subjects were recruited from surgical candidates at the neurosurgery clinic of the BWH, and gave written informed consent to the Partners Healthcare Institutional Review Board (IRB) Protocols. Samples were obtained in cooperation with the BWH Neurooncology Program Biorepository collection, and analyzed under Institutional Review Board-approved research protocol. Human brain tumor samples were dissociated to single-cell suspensions by enzymatic digestion using a brain tumor dissociation kit (Miltenyi Biotec Inc., San Diego, Calif.) and following the automated dissociation protocol using a gentleMACS™ dissociators (Miltenyi Biotec Inc., San Diego, Calif.). Single-cell suspensions were kept at −80° C. in Fetal calf serum (FCS) with 10% DMSO until use.

Chip Preparation.

Chips were cleaned using a Harrick PDC-001 plasma cleaner during 5 min. 1 mL of a 50,000 cells/mL solution was then deposited onto the chips and cells were allowed to settle in the wells for 3 min. A 180° rotation of the chips was done to allow supplementary cells to settle in empty wells for 3 additional min.

The chips were then slanted on a Petri dish and drip-washed 5 to 10 times with 500 μL of PBS 1× to remove the excess of cells at their surface. The cells trapped into the wells were fixed with a 0.25% glutaraldehyde (Fisher Scientific, Pittsburgh, Pa.) solution in PBS 1× at 37° C. during 15 min. Buffer solutions were kept at 37° C. in order to prevent disruption of cells before fixation. After fixation, the chips were washed 5 times during 2 min with Milli-Q water and dried using a MiniArray Microcentrifuge (VWR, Bridgeport, N.J.).

Flow Cytometry.

Cryo-preserved human glioblastoma single-cell suspensions were thawed at room temperature and washed in 10 mL PBS 1×. Fresh glioma samples were also prepared starting from dissociating the samples, as described above, and then proceeding as described here. The tumor suspensions were incubated on ice with Anti-biotin MicroBeads or CD11b MicroBeads (Miltenyi) and run through a magnetic column to remove excess debris or CD11b+ cells from the cell slurry. The cells were split and stained with fluorochrome-labeled mAbs for different known cell populations to be found in tumors. Samples were run on a FACSAria™ II (BD Biosciences) with CellQuest software and analyzed using FlowJo software (Tree Star).

Potential Ab or viability stains to include: A2B5 (Miltenyi); NG2 (BD Bioscience); CD133/1 (AC133) (Miltenyi); 7AAD (BD Pharmigen); and CD45 (clone HI30, Thermo Scientific). Sorted fluorescently labeled cell populations were mixed and applied to the chip as described above for analysis.

Microscopy.

Microscopy Imaging.

Brightfield and fluorescence microscopy images were acquired using an AxioObserver Z1 equipped with an Axio-Cam MRm Rev.3 and a 5×, 0.16 NA objective (Zeiss, Thornwood, N.Y.). For the purpose of these experiments, the microscope has been equipped with a rotating turret of fluorescence filters mounted in cubes and a bright-field reflected light cube was set up with 10:90 UVFS plate beam splitter (Thorlabs, Inc., Newton, N.J.) and an OD 4.0 AR-coated neutral density filter (Thorlabs, Inc., Newton, N.J.) to be able to acquire brightfield and fluorescence microscopy images of the totality of the chips in a single experiment.

Image Processing.

The individual brightfield and fluorescence images were then extracted and downscaled using an in-house MATLAB script. The brightfield and fluorescent channels were artificially colored, overlapped, and the final images were stitched and fused together using the Grid/Collection Stitching plug-in from Fiji/ImageJ on the image processing workstation to generate an .jpeg files used to set up the MALDI MSI experiments in FlexImaging 4.0 software (Bruker Daltonics, Billerica, Mass.).

The microscopy images were also processed using a MATLAB-based software named Enumerator that outputs a .cells.txt file containing a tabulated list of well positions where cells were detected.

Mass Spectrometry Analyses.

Figure 15:
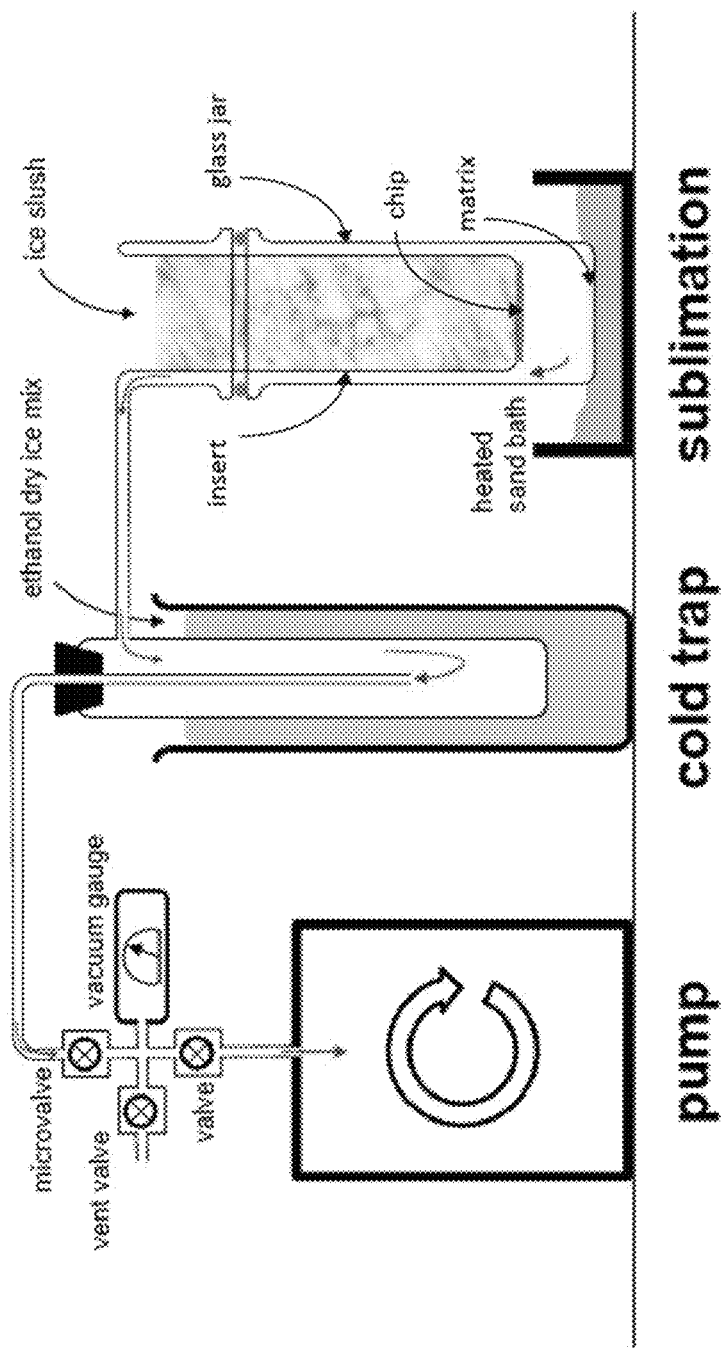
FIG. 15 is a custom sublimation apparatus, used to deposit a MALDI matrix in the plurality of wells.

Matrix Deposition.

α-Cyano-4-hydroxycinnamic acid (CHCA, Sigma Aldrich, St. Louis, Mo.) was deposited onto the chips using a homemade sublimation apparatus as shown in FIG. 15 and as previously described in Chaurand, P.; Cornett, D. S.; Angel, P. M.; Caprioli, R. M., From whole-body sections down to cellular level, multiscale imaging of phospholipids by MALDI mass spectrometry. *Molecular & cellular proteomics*: MCP 2011, 10 (2), O110 004259, which is incorporated herein in its entirety by reference. 300 mg of CHCA matrix was deposited at the bottom of the sublimation apparatus. Protocol was optimized for a fixed vacuum of 7 mTorr, monitoring temperature (160° C.), target plate temperature (4° C.), and time of application (20 min) to ensure a homogeneous matrix coating. Matrix recrystallization was done in a recrystallization chamber as previously described. The recrystallization process was performed in a pre-heated oven at 85° C. during 20 min with a methanol/acetic acid 10% solution (50:50 v/v) pipetted onto a piece of filter paper placed at the bottom part of the recrystallization chamber to create a vapor for the recrystallization process.

Registration.

Figure 9:
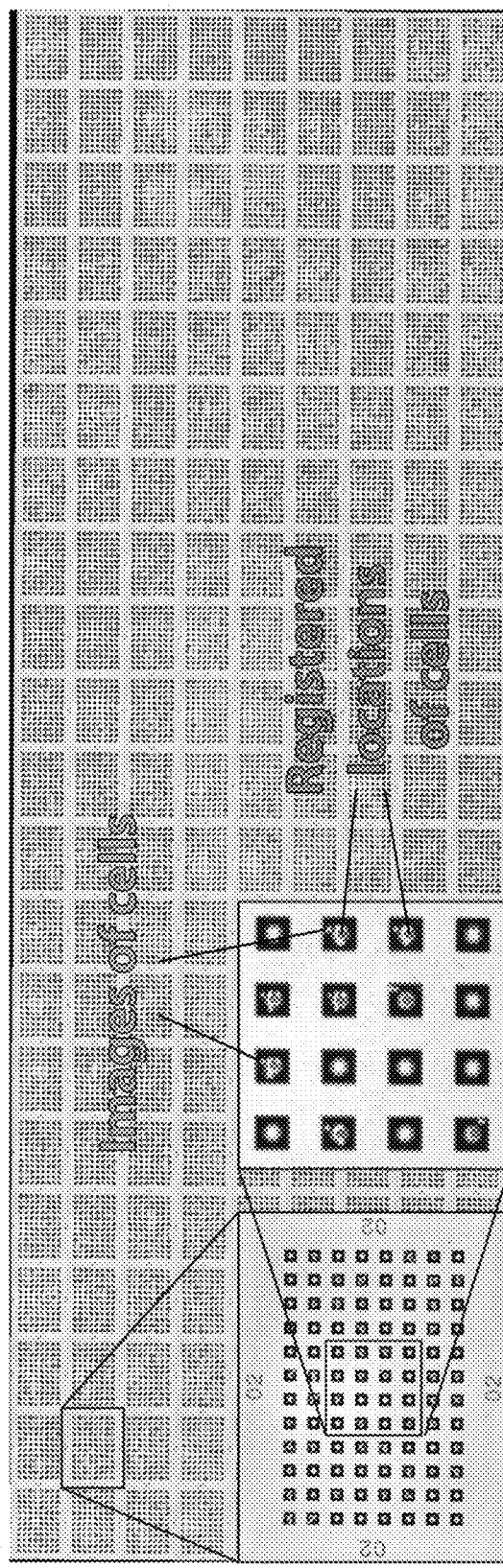
FIG. 9 is an example of a map having the absolute positions of the wells of the device, the imaged positions of cells within the wells, and the calculated positions of cells for MALDI, according to one aspect of the present disclosure.

The chip was mounted in a specimen holder (designed to accommodate microscope slides) and was placed in the MALDI instrument. With the help of an in-house MATLAB script, the individual images of the blocks were extracted and downscaled from ZEN file, the fluorescent and brightfield channels were artificially colored and were overlapped, and the final images were stitched and fused together using the Grid/Collection Stitching plug-in from Fiji/ImageJ on the image processing workstation. The final uncompressed size of the image was set to no more than 200 MB to be compatible with MALDI imaging software flexImaging 4.0 (Bruker Daltonics). The image was also flipped in ImageJ to show the actual (not mirrored as imaged) surface of the chip, where the labeling numbers were readable. In several instances of the experiment, stitching missed a corner block, in which case ImageJ was used to draw the position of the corner well of that block. A "Tissue Profiling" experiment was initiated in flexImaging and, using the live window, navigated to the corner wells of 3 corner blocks on the chip, and matched them to those in the image. The dummy experimental XML file containing this calibration information, along with the '.cells' file from Enumerator and the stitched image file, were then imported into a custom Python script that calculated the absolute positions of all the wells with the cells, along with a fraction of empty wells, and added them to the XML file, displaying the results as dots on the image for visual inspection, as shown in FIG. 9. Green dots represent images of the cells and blue dots represent the registered locations of the cells. The updated XML file was then imported back to flexImaging.

MALDI Mass Spectrometry Imaging.

MALDI-MSI analyses were set up using FlexImaging 4.0 software in tissue profiling mode with a laser probe spot diameter of 50 μm to match the size of the bottom of the wells. The dummy experimental .mis file containing the teach points used to map image coordinates to sample carrier positions, along with the .cells.txt file created using Enumerator, and the stitched image files were then imported into a custom Python script to calculate the absolute positions of the wells containing cells and add them to the .mis file. Positions corresponding to empty wells were also added to be used as negative control.

MALDI-MSI analyses were performed using an UltrafleXtreme MALDI TOF/TOF mass spectrometer (Bruker Daltonics, Billerica, Mass.) equipped with a 1 kHz smartbeam laser. Mass spectra were acquired in reflectron positive ion mode between m/z 300 to 1,000 and externally calibrated using a small molecule calibration standard solution. The laser intensity was set to 30% and 1000 laser shots were accumulated per position with a random walk limited to a diameter of 100 μm. The laser beam was manually offset to compensate for the variation in height between the bottom and top surfaces of the wells. MSI data were analyzed with FlexImaging 4.0 software.

Figure 10:
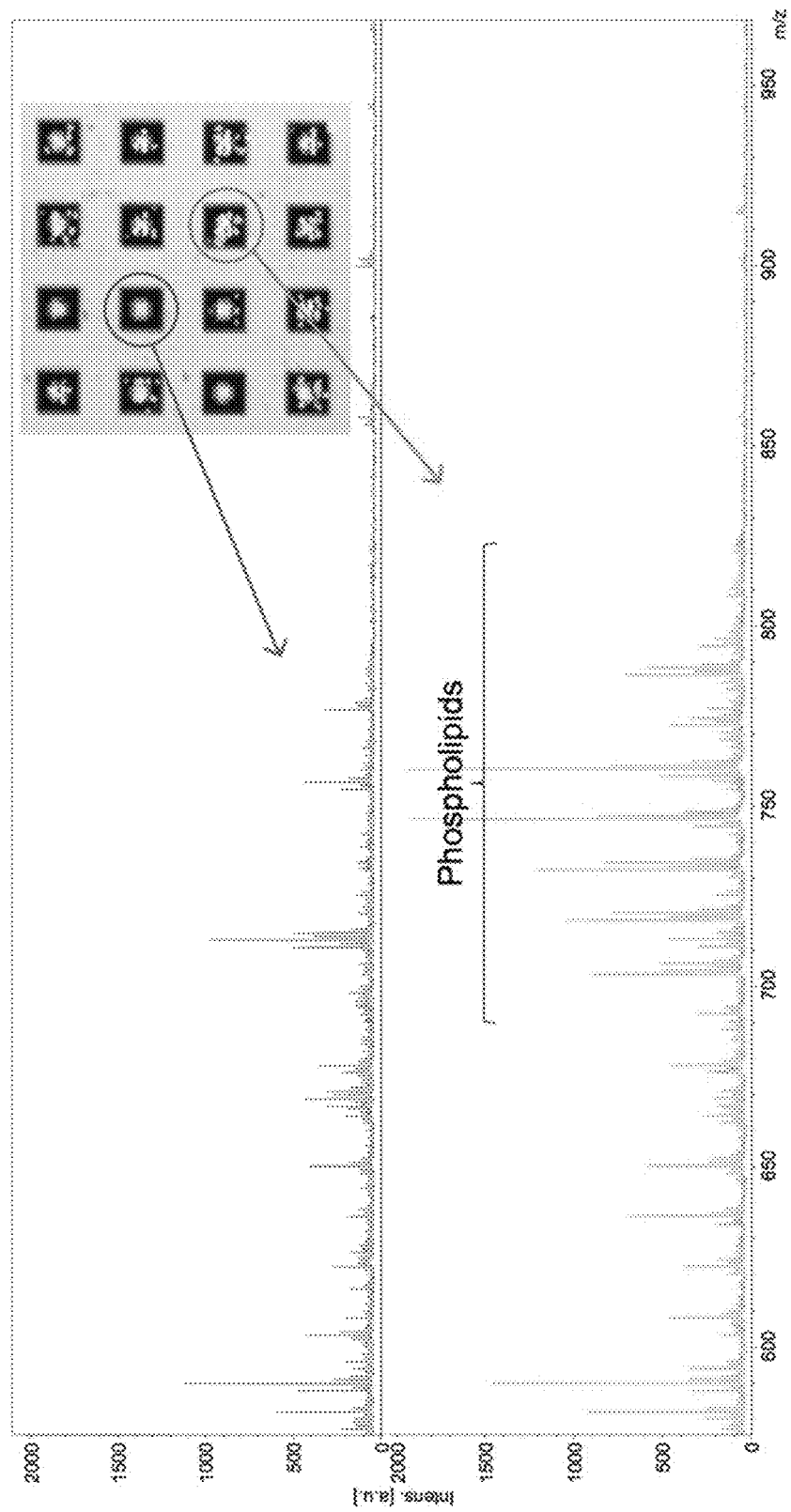
FIG. 10 contains plots showing mass spectra for empty wells (gray) compared with wells containing a cell (green).
Figure 11:
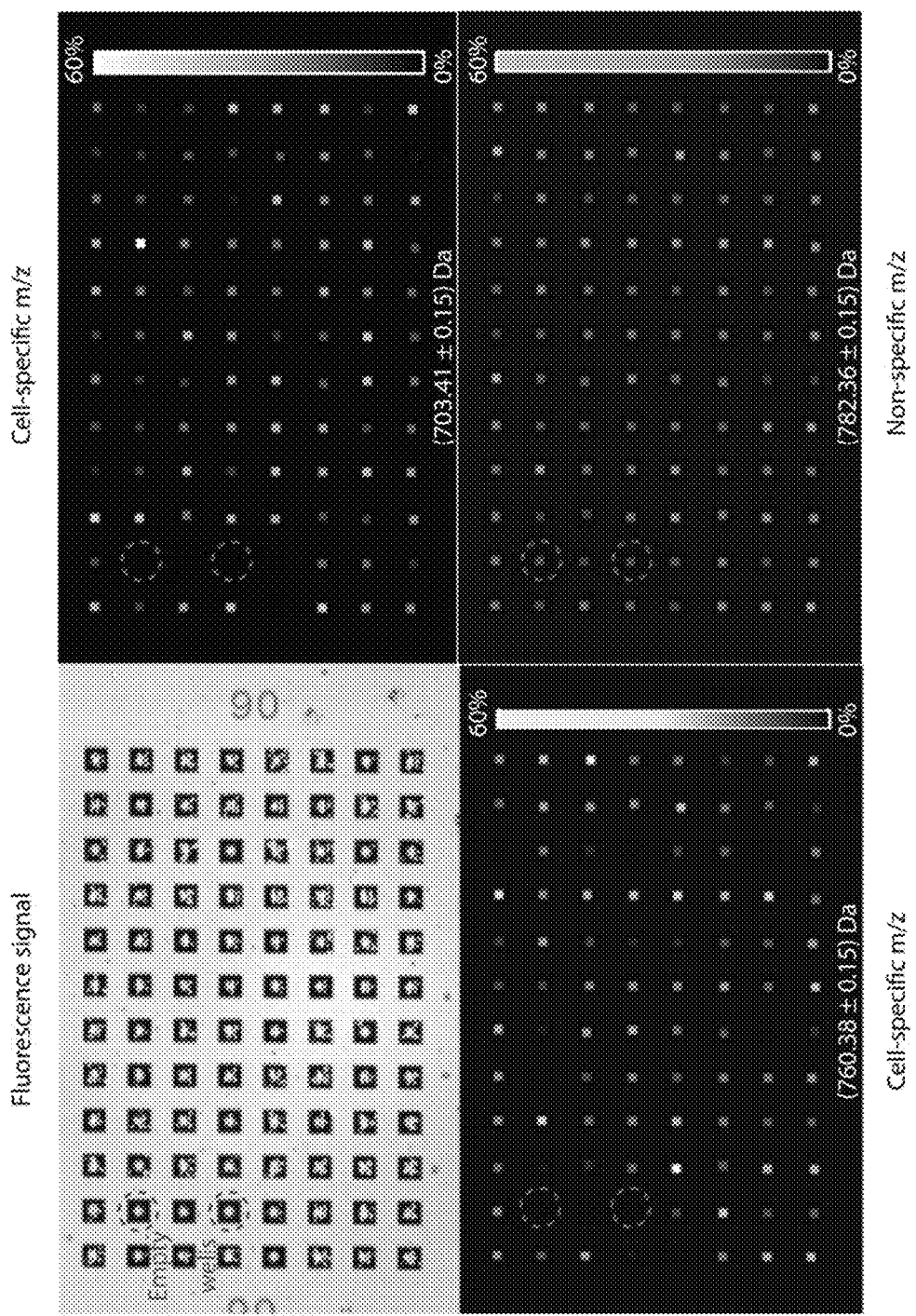
FIG. 11 contains a fluorescence signal (top-left), two cell-specific MALDI signals (top-right and bottom-left), and a non-specific MALDI signal for a plurality of wells.

MS analysis started with a manual observation of characteristic peaks in the region of interest (e.g. 700-800 Da for phospholipids) for the spectra located on wells with the cells as compared to empty wells. The peaks present in the former but absent in the latter (FIG. 10) were then visualized on the image of the chip, with mass filters set to +/−0.1 Da (FIG. 11), to confirm correlation with the presence of cells. Alternatively, the peaks of interest could have been identified from the previous experiments and/or the literature. For each peak, its intensity across all the wells could be exported as a list.

Figure 12:
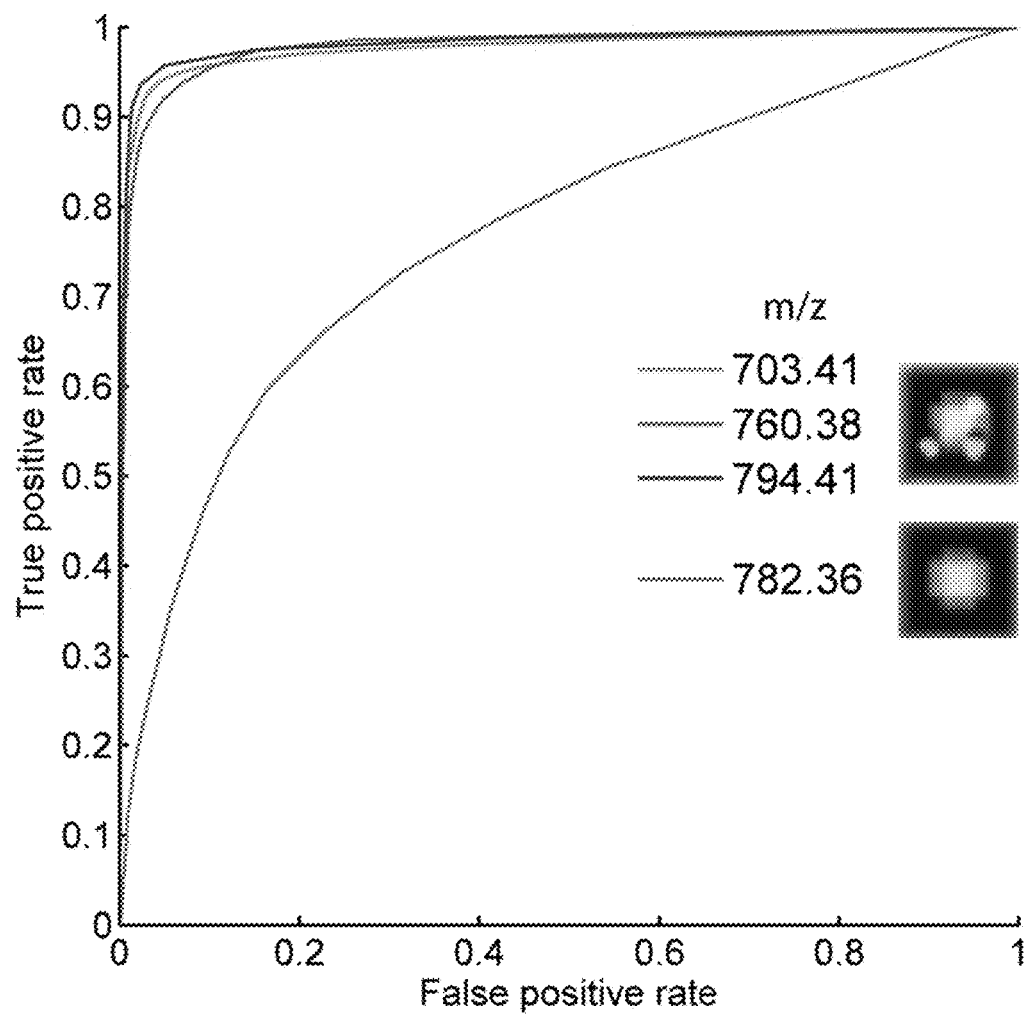
FIG. 12 is a receiver operating characteristic (ROC) curve for MALDI signal compared with fluorescence as the gold standard.
Figure 13A:
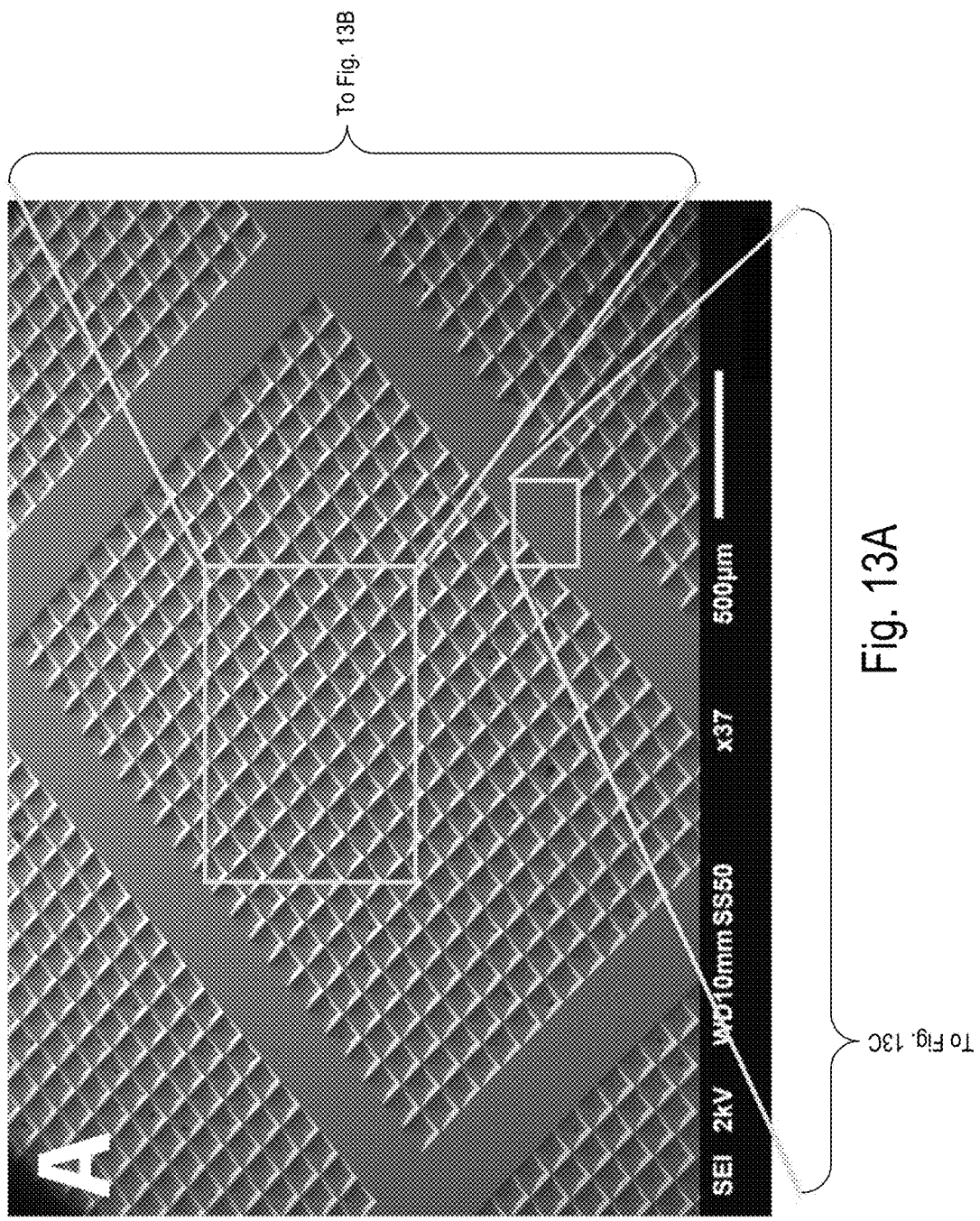
FIG. 13A is a zoomed image of the device shown in FIG. 2.
Figure 13B:
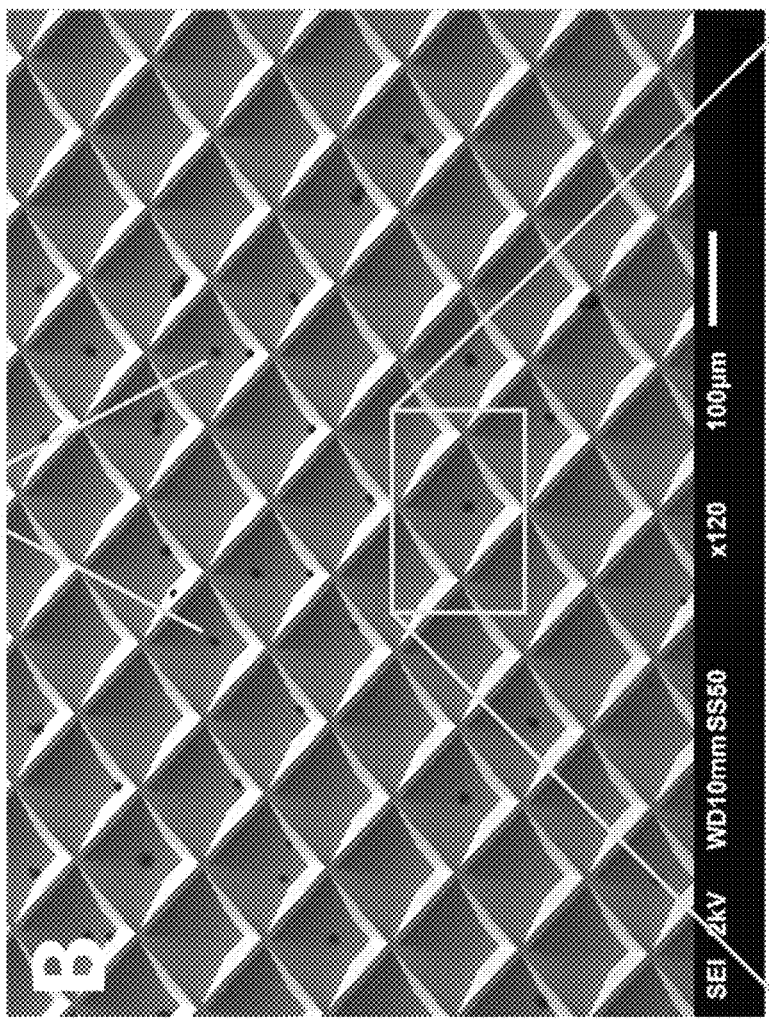
FIG. 13B is a zoomed image of the device shown in FIG. 2.
Figure 13C:
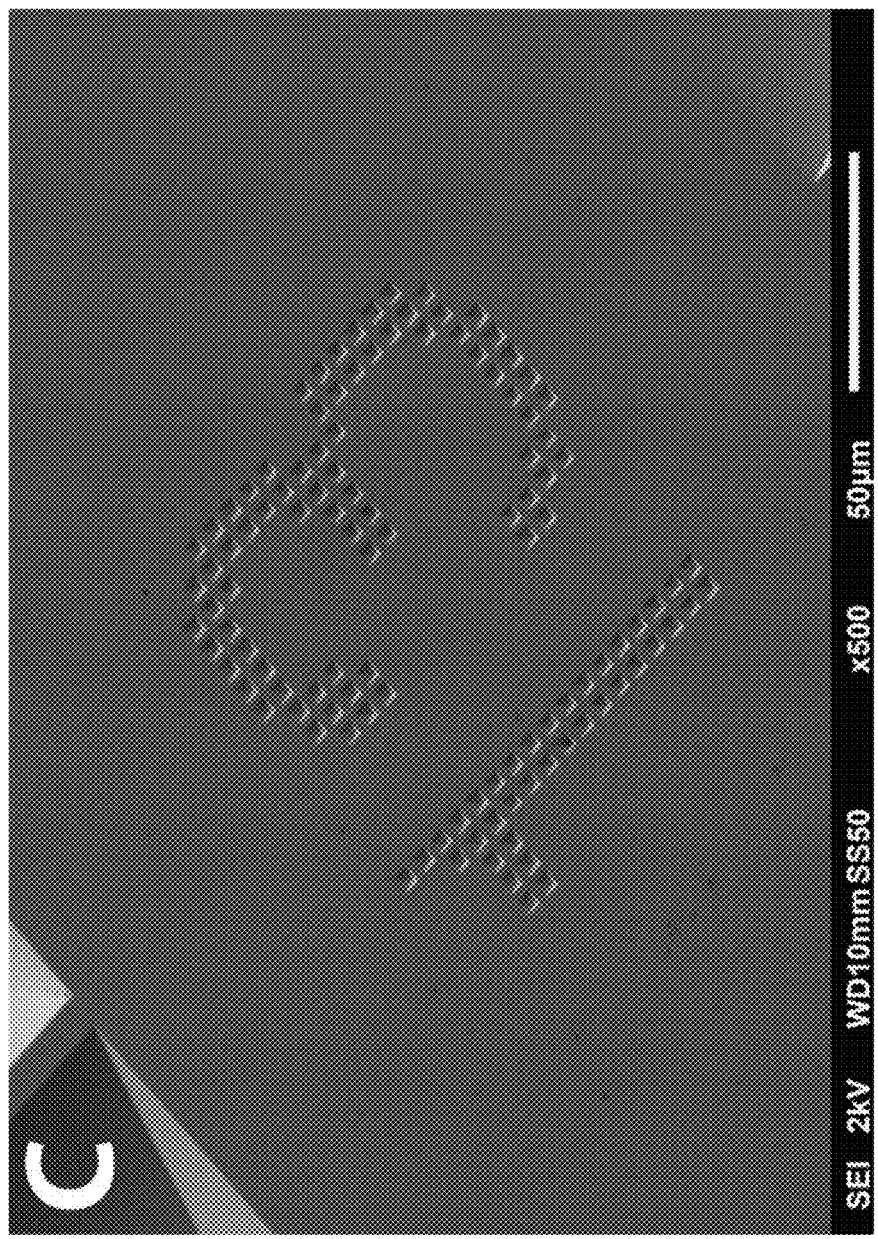
FIG. 13C is a zoomed image of the device shown in FIG. 2.
Figure 13D:
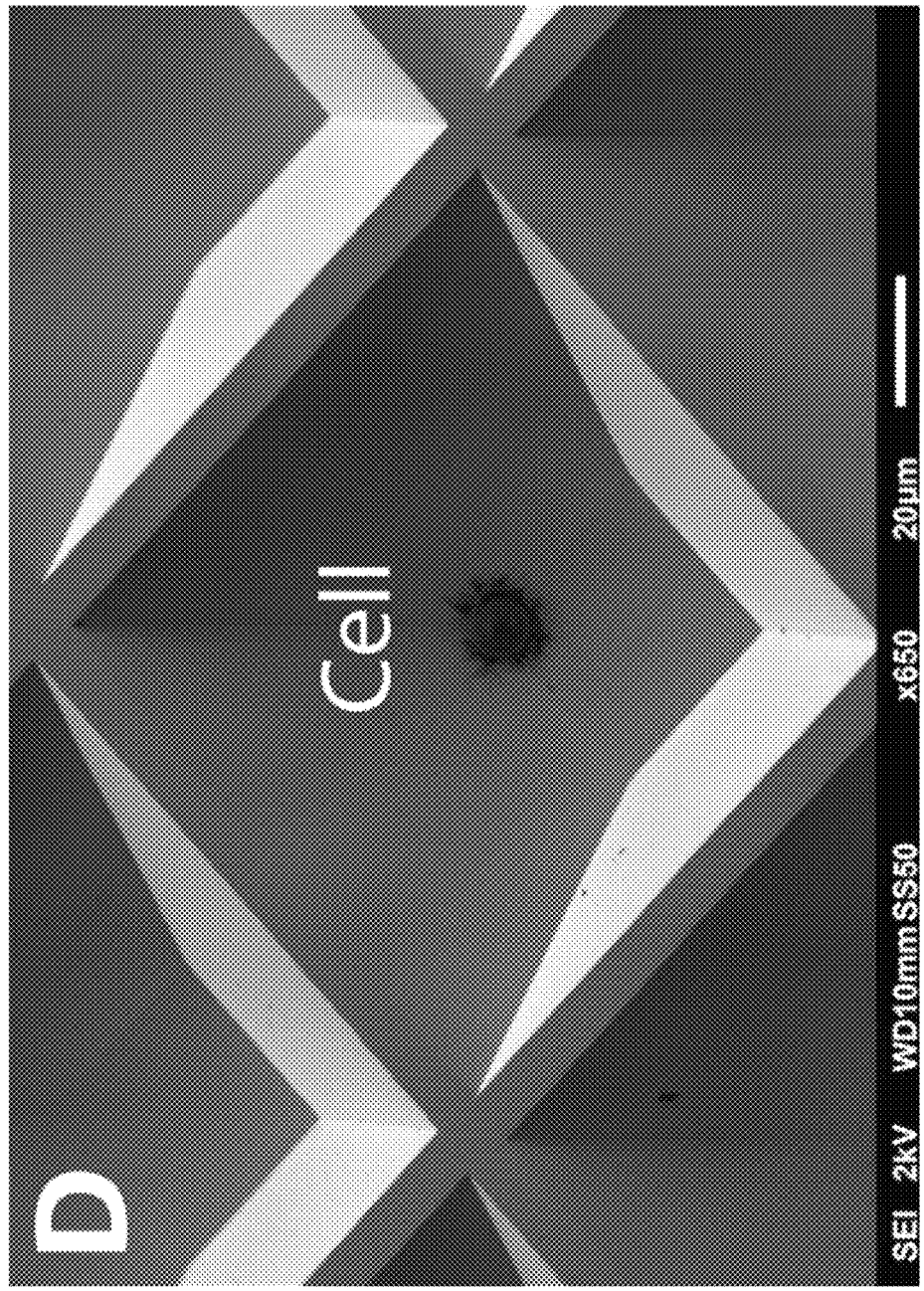
FIG. 13D is a zoomed image of the device shown in FIG. 2.

To plot a ROC curve for MALDI signal with fluorescence as the gold standard (FIG. 12), the true positive rate $TPR=TP/(TP+FN)$ was calculated, where TP were true positives (number of wells with both fluorescence and MALDI signal above a threshold), FN were false negatives (wells with fluorescence but no mass signal), versus false positive rate $FPR=FP/(FP+TN)$, where FP were false positives (no fluorescence but mass signal above a threshold) and TN were true negatives (no fluorescence, no mass signal), for varying thresholds.

Statistics.

PCA was performed from the mass spectra acquired during each experiment. Analyses were conducted using ClinProTools version 3.0 (Bruker Daltonics, Billerica, Mass.) using level scaling, peaking on total average spectrum, no peak limits, peak calculation by intensities, and an m/z range of 600-1200.

Cleaning.

Cleaning of chips from matrix and cells or their residues was attempted using an in-house protocol previously used for tissue samples fixed to ITO-coated slides. Briefly, the chips were loaded in a metallic holder for glass slides and sonicated in acetone for 15 min. After rinsing 2 times with water, the chips were sonicated further in 5% Micro-90 cleaning solution (Cole-Parmer) for 15 min. After rinsing in water again until no bubbles from Micro-90 remained, the chips were sonicated in water for 5 more min, then in methanol for 15 min, and finally in water again for 15 min.

Example 1

Isolating Cells and Performing MALDI-MSI in Si-Based Device

A Si-based device was prepared in accordance with the methods described above. Briefly, the following steps were performed: a suitable mask was designed, which was then photolithographically used to define arrays of wells and registration marks on Si wafers; cells were prepared in suspension and loaded into the wells of the chip; the array was imaged using an automated fluorescence microscope;

images were processed to identify the location of wells including one and only one cell; a MALDI matrix was deposited using a sublimation protocol; a global "map" of the entire chip was generated, for navigation with the MALDI imaging software, including the global positions of wells of interest defined with respect to corner points on the "map"; automated MALDI spectra were acquired at wells of interest, as well as at control wells; and the spectra were analyzed to define peaks of interest and relate said peaks back to the fluorescence signal. An image of the Si-based device is shown in FIG. 2, with the image in various levels of zoom shown in FIGS. 13A, 13B, 13C, and 13D.

The protocol for processing of cells was developed using cultured cell lines. Before loading cells into the wells, the chip was placed in a plasma cleaner to promote removal of organic residues and make the surface more hydrophilic. The cells were stained and re-suspended in PBS to reduce the amount of background signal coming from the culture media or blood; cell concentration was adjusted such that the total number of loaded cells would match several times the number of wells on the chip, to ensure efficient distribution of cells across the wells. The suspension of cells was spread across the chip and, after a short incubation, the excess was washed away by gently dispensing PBS from the short edges of the tilted chip; loaded cells remained trapped in the wells. Reflection-mode fluorescence microscopy was performed on the plurality of wells. Since an inverted setup was used for fluorescence microscopy, the cells were fixed in the wells to prevent them from falling when imaging face down.

Fluorescence imaging was performed in an automated fashion using a pre-determined list of positions corresponding to locations of the blocks on the chip. Support points were defined by focusing at the bottom of the wells for several locations in the array, and spline interpolation of these points was relied upon for all the positions in the list. To define the locations of the wells for subsequent image analysis, bright-field (non-fluorescent) images of the blocks were acquired; a wide-band dichroic mirror was used to pass the excitation light (reflected from the sample) to the camera, and its intensity was adjusted with a neutral density filter. Finally, the magnification of the microscope was adjusted to considerably reduce the amount of time spent on imaging, with minimal loss in resolution; this was possible because the camera had a high pixel count and low pixel size, and high resolution is not required for these applications.

Figure 14:
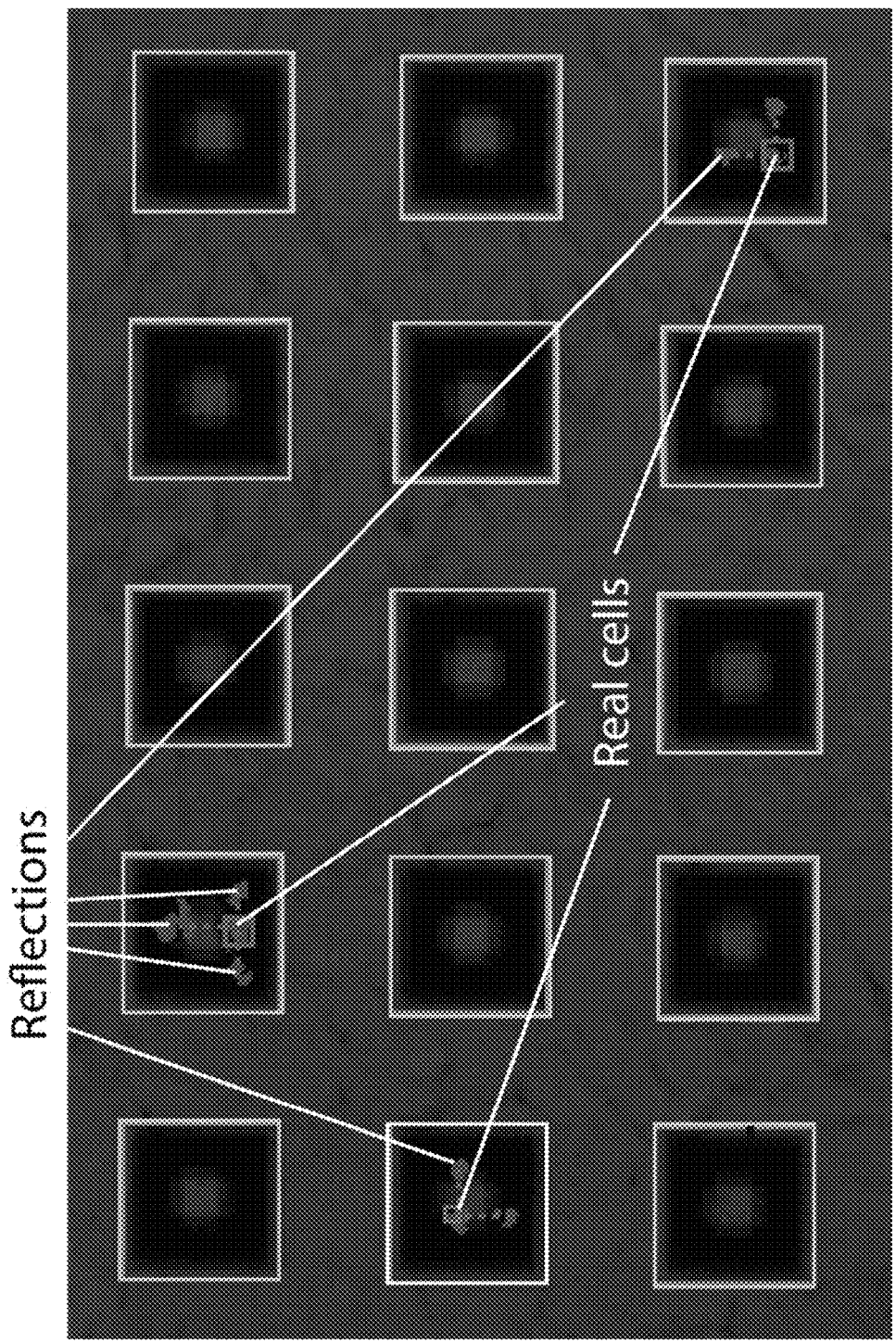
FIG. 14 is a fluorescence image of a plurality of wells, showing reflections from the side walls of the well, and a calculated location of cells, as described in Example 1.

Images of individual blocks were subsequently processed with a version of in-house automated image analysis software (Enumerator), modified to correctly detect pyramidal wells. The slanted walls of the wells were highly reflective, producing mirror images of each cell in the 4 walls of a well, as shown in FIG. 14. The mirror images had a specific pattern (forming a "cross" around each cell), which could be used to deduce the real locations of the cells if sub-well localization was required.

To prepare the chip for molecular imaging in a MALDI instrument, we needed to deposit a matrix layer on top of the cells. One of the methods of matrix deposition most suitable to this analysis is sublimation with re-crystallization. A custom sublimation apparatus (shown in FIG. 15) and an optimized procedure were created to ensure a homogeneous layer of matrix, as described in the METHODS section above. This layer was also re-crystallized in a solvent-humidified chamber to partially incorporate the analytes of interest (i.e. phospholipids) into the matrix crystals.

For registration in the MALDI instrument's control software (flexImaging), a single composite image of an entire chip is required. A stitching plugin from ImageJ was used in a custom script to piece together the images of individual blocks (provided with pre-engineered overlap area and numbering) with sub-pixel accuracy. Along with excellent dimensional stability of Si, this allowed registration of wells with high precision, potentially suitable even for sub-well navigation.

To generate a list of positions to be acquired by MALDI, an XML file with calibration information from flexImaging was exported, and the file was parsed using a custom Python script to add the list of wells with cells as defined by Enumerator, along with a randomized list of empty wells used for control. An example map of the chip with added positions is shown in FIG. 9, and the procedure for acquisition of MALDI signal is described in the METHODS section.

The detection of phospholipid signal in MALDI was compared to the detection of fluorescence signal as the gold standard. Mouse fibroblast cells expressing enhanced green fluorescent protein (eGFP) were loaded onto an array, and wells containing cells were identified through fluorescent imaging. Occupied wells, along with a random sample of empty wells, were then subjected to MALDI analysis. Receiver operating characteristic (ROC) curves (FIG. 12) suggest a high degree of correlation between fluorescent and MALDI signal for many m/z values that were handpicked by a trained specialist from the MALDI spectra.

Figure 18:
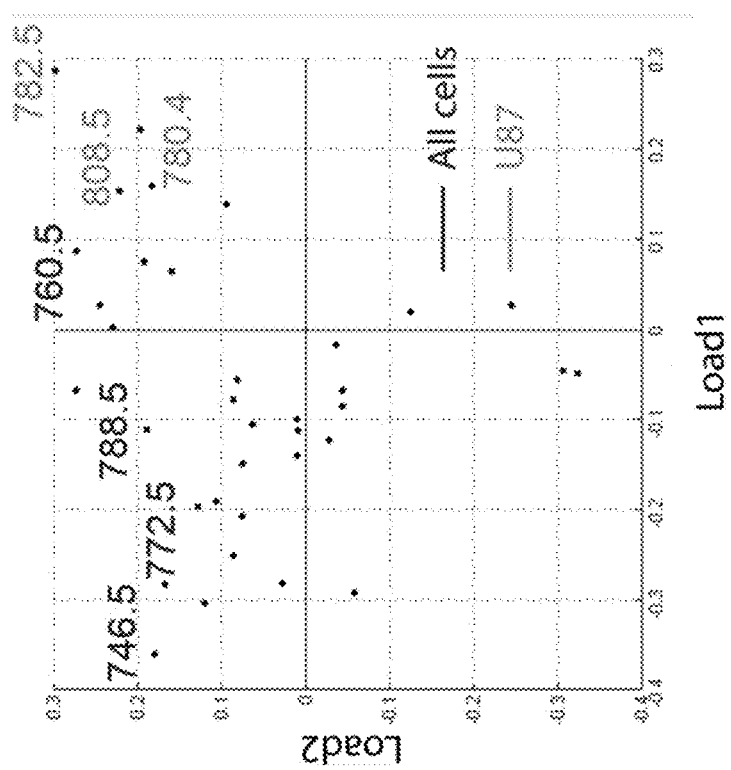
FIG. 18 is a principle component analysis plot for certain mass peaks, as described in Example 1.
Figure 17:
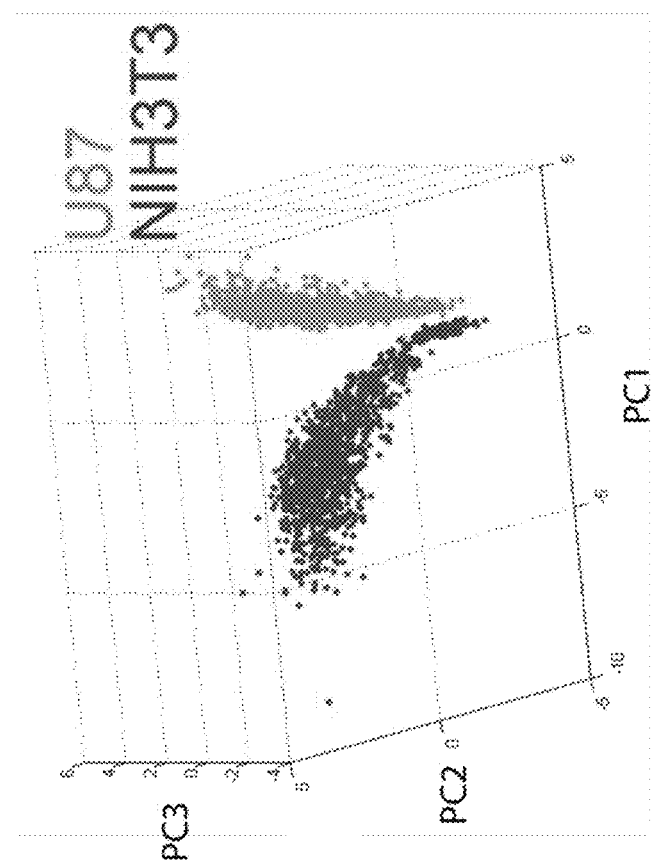
FIG. 17 is a principle component analysis plot showing segregation of two cell lines, as described in Example 1.
Figure 19:
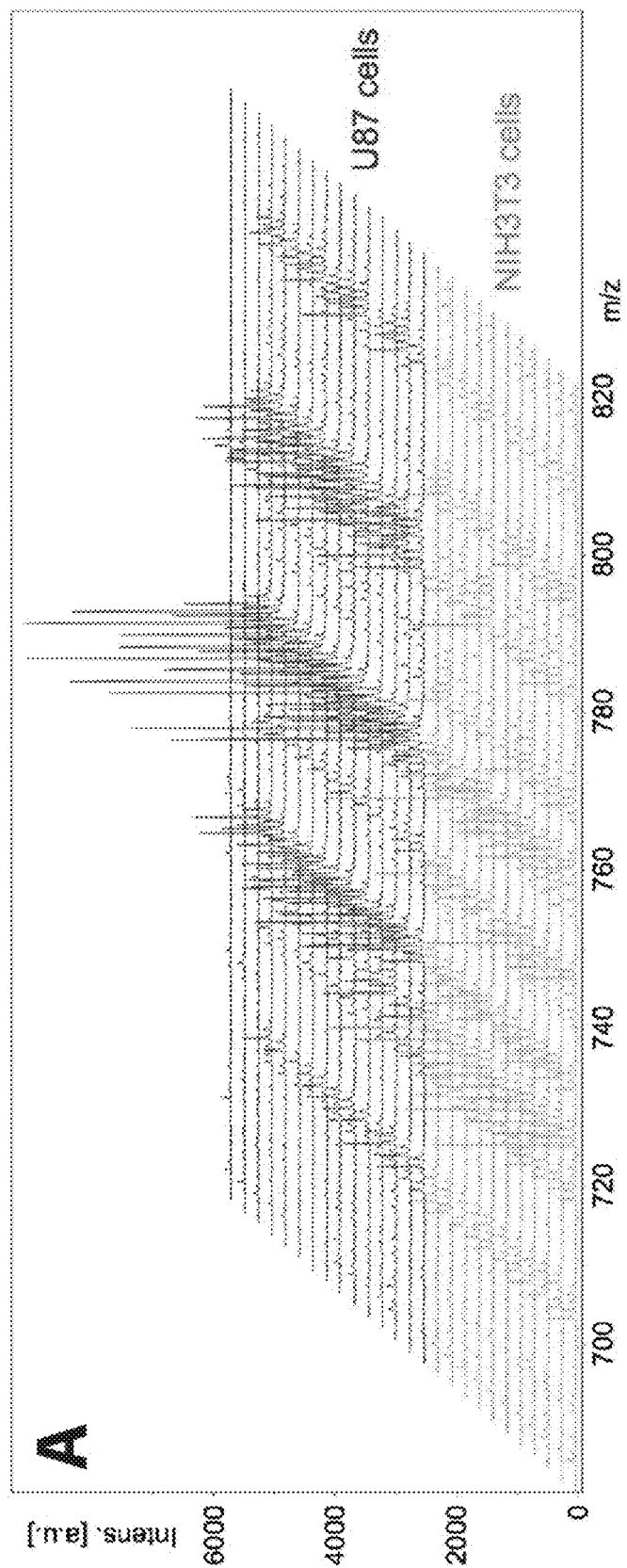
FIG. 19 shows MALDI spectra for two lines of cells processed on a single chip, as described in Example 1.
Figure 20:
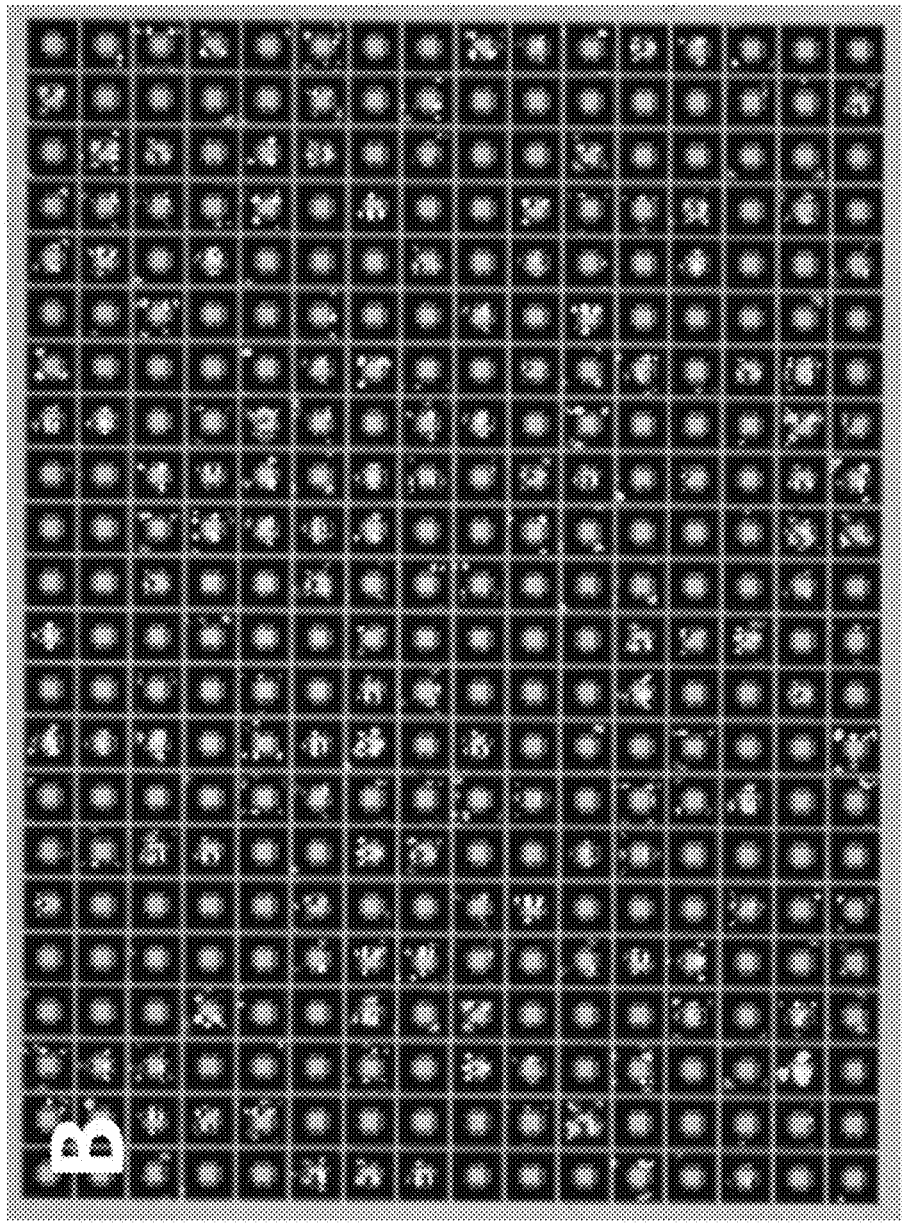
FIG. 20 shows fluorescence images of two lines of cells on a single chip, the two lines of cells having different fluorescence markers, as described in Example 1.
Figure 21:
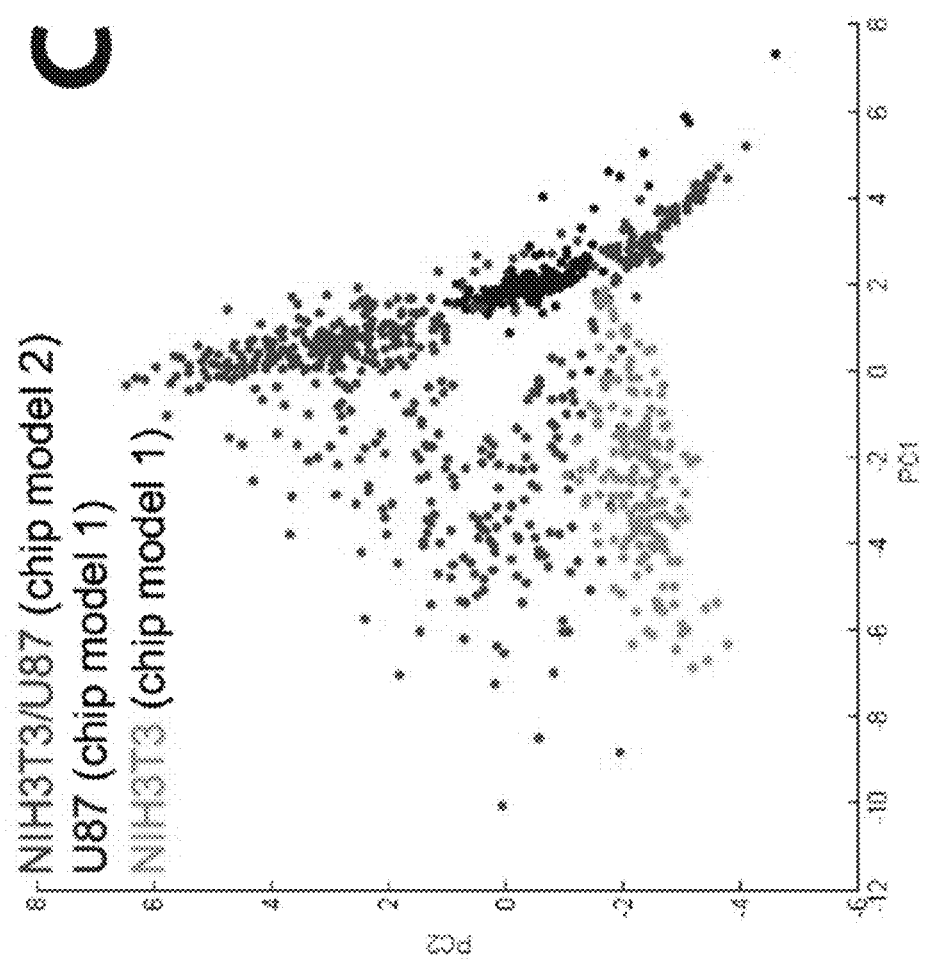
FIG. 21 is a principle component analysis score plot of two cell lines processed on separate chips (blue and green) or on a single chip (red), as described in Example 1.

The ability to use single cell MALDI spectra to identify unique cell populations was then investigated. The phospholipid profiles of two distinct cell lines were processed on separate chips. The results are shown in FIG. 16, where the visualization of matrices of the phospholipid signal (700-860 Da, horizontally) across 1152 spectra (vertically) for each of U87 cells (FIG. 16A) and NIH3T3 cells (FIG. 16B) is shown. Principle component analysis (PCA) successfully segregated the two cell lines, as shown in FIG. 17. The analysis also revealed characteristic peaks that could serve as cellular signatures, as shown in FIG. 18. The peaks in blue could be identified as phospholipid markers of cellularity, while the peaks in orange could be associated with U87 cells. The two cell populations were then mixed and processed on a single chip. The results are shown in FIGS. 19-21 and confirm that distinct cell lines can be identified based on the signatures. FIG. 19 shows MALDI spectra for two lines of cells processed on a single chip. FIG. 20 shows the cells as visualized in the fluorescence microscope, where the U87 stained with DAPI are shown in blue and the NIH3T3 expressing eGFP are shown in green. FIG. 21 is a PCA score plot of the two populations processed on separate chips (blue and green) or on a single chip (red). U87-specific signal (m/z 760.4, 782.4, and 808.4) can be detected from the mixture.

Figure 22:
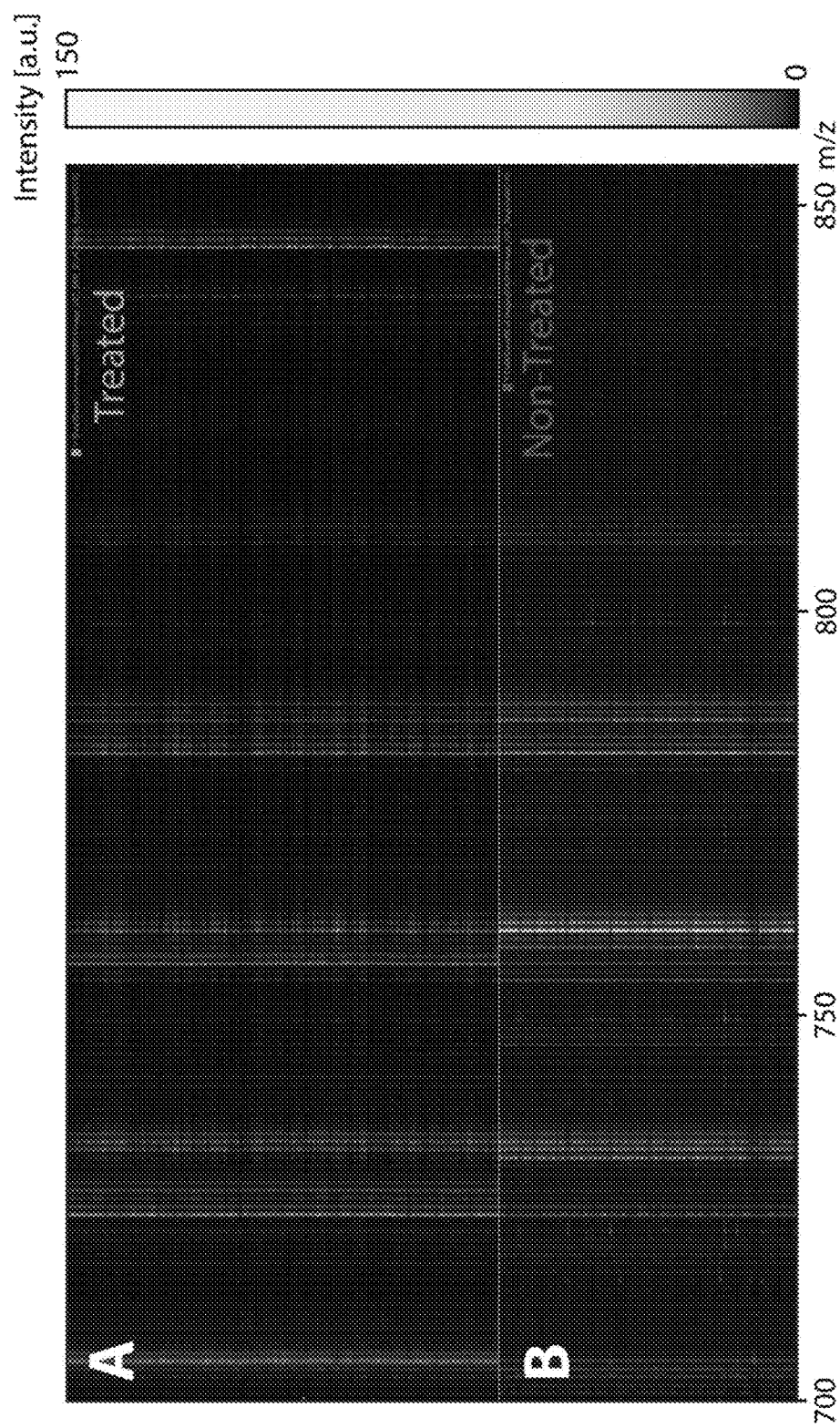
FIG. 22 is a comparison between 280 mass spectra of drug-treated U87 cells (A) and 192 mass spectra of non-treated cells (B), as described in Example 1.
Figure 23:
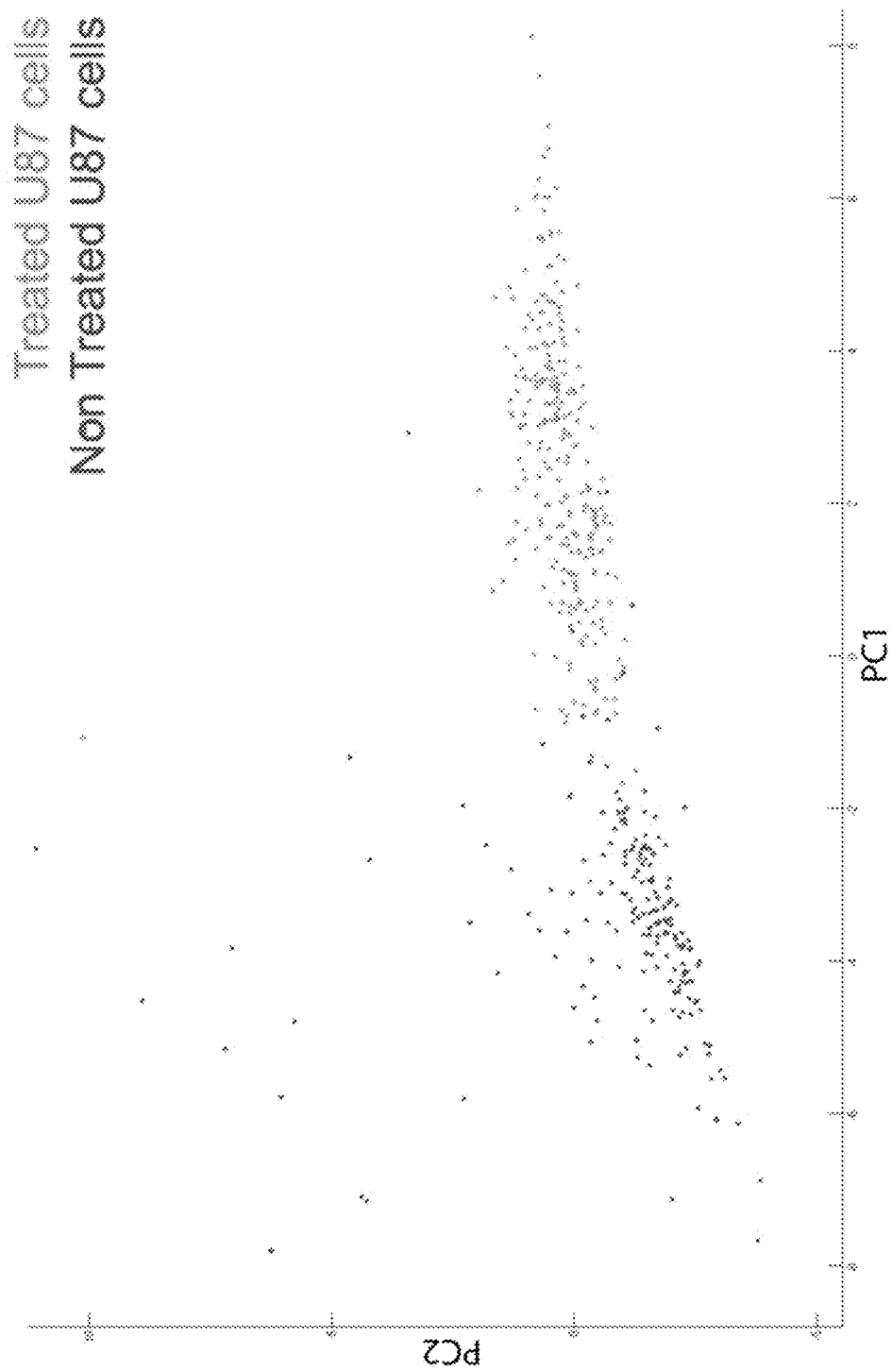
FIG. 23 is a principle component analysis score plot illustrating distinct populations, namely drug-treated and non-treated, as described in Example 1.

To demonstrate the ability of the assay to identify unique primary cell populations, human primary glioblastoma cell line (U87-MG) was analyzed pre- and post-treatment with lipid kinase inhibitor BKM120, utilizing separate chips for processing. This potent drug penetrates the blood-brain barrier and acts on class I phosphatidylinositol-3-kinase (PI3K) intracellular pathway implicated in many cancers, including glioblastoma; along with its metabolites, this small molecule drug can be imaged directly (i.e. without further labeling) with MALDI MSI. The cells were imaged in the same m/z window as the two lines from above. Using this technique, treated and untreated cells were successfully segregated, demonstrating the ability to estimate the effect of defined perturbation (drug treatment) on the phospholipid profile of a given population of cells. FIG. 22 shows a comparison between 280 mass spectra of drug-treated U87 cells (FIG. 22A) and 192 mass spectra of non-treated cells (FIG. 22B). FIG. 23 is a PCA score plot illustrating two distinct populations, namely, treated and non-treated cells.

Example 2

Isolating Cells and Performing MALDI-MSI in Plastic-Based Device

A plastic-based device was prepared in accordance with the methods described above. Briefly, a cyclic olefin polymer containing a plurality of wells was prepared, according to the methods described above. In order to retain a substantially transparent device, while applying a MALDI-compatible surface, a thin layer of ITO (~120 nm) or gold (~20 nm, with Ti for adhesion) was applied to the surface. A plurality of cells was introduced into the plurality of wells, fluorescence microscopy was performed, and MALDI-MSI was performed, in accordance with the methods described herein.

Example 3

Isolating Cells and Transferring to MALDI-Active Slide

Figure 24:
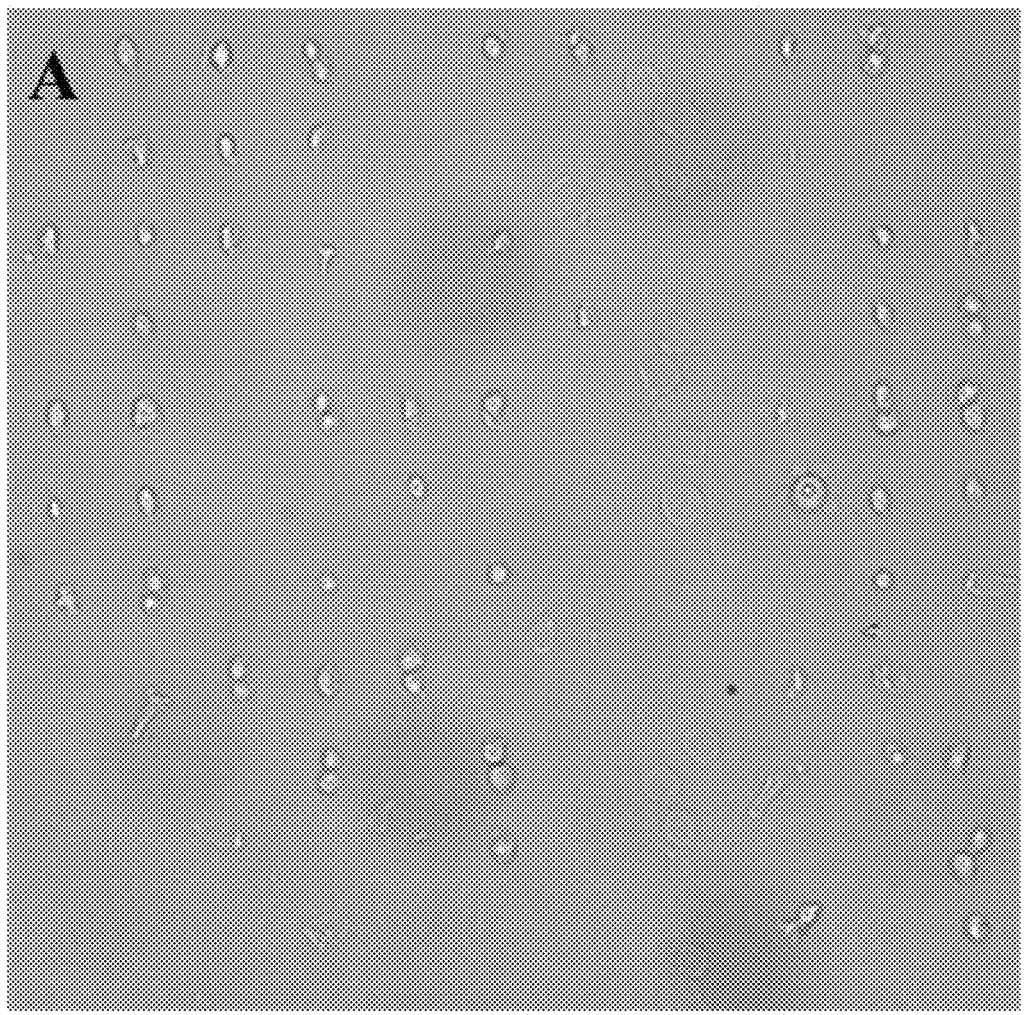
FIG. 24 is an image of cells transferred to an ITO-coated slide after being isolated in a plurality of wells, in accordance with the present disclosure and as described in Example 3.

A PDMS-based microwell array having a 30 μm well size was formed in accordance with the methods described above and methods described in U.S. Patent Application Pub. No. 2011/0124520 ("the '520 Pub."), which is incorporated herein in its entirety by reference. Non-polar polyethylene glycol (PEG) molecules were attached to the surface of the microwell array by way of PEG-g-PLL, a graft copolymer of PEG with poly-L-lysine, and temporary oxidation of the PDMS surface, as described in M. Morra, E. Occhiello, R. Marola, F. Garbassi, P. Humphrey, and D. Johnson, "On the aging of oxygen plasma-treated polydimethylsiloxane surfaces," *J. Colloid Interface Sci.*, vol. 137, no. 1, pp. 11-24, June 1990, which is incorporated herein in its entirety by reference. Cells were introduced to the microwells in accordance with the methods described above and methods described in the '520 Pub. An ITO-coated glass slide was conformally sealed together with the PDMS-based microwell array using a metal clamp with a tightening screw. The sealed array was centrifuged at 1000 rpm (~200 g) for five minutes to transfer the cells from the microwells onto the ITO-coated glass slide. FIG. 24 is an image of cells transferred to the ITO-coated glass slide was acquired on a Zeiss AxioObserver Z1 at 10× with 800 μm field of view.

Prophetic Example 4

Si-Based Device with Transparent Well Bottoms

A version of the device described herein will be formed, whereby the wells are fabricated in silicon, thus preserving their shape, but the bottom will be formed by a transparent glass substrate (e.g., Pyrex®) that is anodically bonded to the silicon wafers. The conductive layer will be formed by thin-film deposition of ITO or gold. The device can be fabricated according to the methods described in S. Lindstrom, R. Larsson, and H. Andersson-Svahn, "Towards high-throughput single cell/clone cultivation and analysis," Electrophoresis, vol. 29, no. 6, pp. 1219-1227, 2008, which is incorporated herein in its entirety by reference.

The invention has been described in connection with what are presently considered to be the most practical and preferred embodiments. However, the present invention has been presented by way of illustration and is not intended to be limited to the disclosed embodiments. Specifically, the above specific methods used are exemplary of the inventive concept and may be altered while still falling within the scope and spirit of the invention. Accordingly, those skilled in the art will realize that the invention is intended to encompass all modifications and alternative arrangements within the spirit and scope of the invention as set forth in the appended claims.

We claim:

1. An isolated cell analysis device comprising a substrate having a first surface comprising a plurality of wells,
   the first surface comprising the plurality of wells configured to receive a suspension comprising a plurality of cells, the suspension has a concentration of cells of between 1000 cell/mL and 500,000 cells/mL,
   the plurality of wells configured to have at least 25% of the wells contain one and only one cell upon receiving the suspension comprising a plurality of cells, waiting a length of time to allow the plurality of cells to settle, and removing an excess of the suspension from the first surface,
   each of the plurality of wells has side walls that have an inward slope of between 10 degrees and 80 degrees relative to the first surface,
   each of the plurality of wells having one or more of the following properties:
   a depth of between 1 μm and 250 μm;
   an opening in the first surface with a diameter of between 10 μm and 100 μm;
   an opening in the first surface with an area of between 100 μm$^2$ and 10,000 μm$^2$; and
   a volume of between 1 pL and 10 nL, and
   each of the plurality of wells configured to allow an isolated cell contained within one of the plurality of wells to be optically interrogated and to subsequently have the isolated cell contained within one of the plurality of wells be ionized by matrix assisted laser desorption ionization via a laser impinging on the isolated cell at an angle between 5 and 85 degrees relative to the first surface.

2. The device of claim 1, wherein the substrate comprises a material selected from the group consisting of silicon, polydimethyl siloxane, cyclic olefin polymer, polypropylene, poly(methyl methacrylate), polystyrene, a conductive metal, indium tin oxide, a III-V semiconductor, and combinations thereof.

3. The device of claim 1, wherein each of the plurality of wells has side walls that have an inward slope of between 15 degrees and 75 degrees relative to the first surface.

4. The device of claim 1, wherein each of the plurality of wells has at least one matrix-assisted-laser-desorption-ionization-compatible (MALDI-compatible) surface.

5. The device of claim 4, wherein the at least one MALDI-compatible surface comprises a material selected from the group consisting of indium tin oxide, a conductive metal, a III-V semiconductor, and combinations thereof.

6. The device of claim 1, wherein each of the plurality of wells has a depth of between 1 μm and 250 μm.

7. The device of claim 1, wherein each of the plurality of wells has an opening in the first surface with a diameter of between 10 μm and 100 μm.

8. The device of claim 1, wherein each of the plurality of wells has an opening in the first surface with an area of between 100 µm² and 10,000 µm².

9. The device of claim 1, wherein each of the plurality of wells has a volume of between 1 pL and 10 nL.

10. The device of claim 1, the device further comprising a registration mark located on the first surface.

11. The device of claim 1, the device further comprising a calibration area in the first surface, the calibration area having a depth that is that is equal to a depth of the plurality of wells.

12. A method of making a single cell analysis device, the method comprising:

forming a pattern of a plurality of wells in a first surface of a substrate, each of the plurality of wells configured to allow an isolated cell contained within one of the plurality of wells to be optically interrogated and to subsequently have the isolated cell contained within one of the plurality of wells be ionized by matrix assisted laser desorption ionization, each of the plurality of wells having side walls that have an inward slope of between 10 degrees and 80 degrees relative to the first surface; and applying a matrix-assisted-laser-desorption-ionization-suitable (MALDI-suitable) material to at least a portion of each of the plurality of wells in the substrate.

13. The method of claim 12, wherein the forming a pattern step comprises:

depositing a nitride coating on the substrate;

applying a photoresist to the nitride coating on the first surface of the substrate;

forming the pattern of the plurality of wells in the photoresist;

etching the pattern into the nitride coating;

removing the photoresist that remains on the first surface;

forming the plurality of wells at the locations where the nitride coating has been removed in the etching the pattern step; and removing the nitride coating that remains on the first surface.

14. A method of optically interrogating and subsequently matrix assisted laser desorption ionizing a plurality of isolated cells, the method comprising:

isolating a plurality of cells in a plurality of wells, such that at least 25% of the plurality of wells contain one and only one cell of the plurality of cells;

optically interrogating at least a portion of the plurality of isolated cells located in the plurality of wells containing one and only one cell;

introducing a matrix assisted laser desorption ionization matrix into the plurality of wells; and matrix assisted laser desorption ionizing the at least the portion of the plurality of isolated cells located in the plurality of wells containing one and only one cell.

15. The method of claim 14, wherein the isolating a plurality of cells in a plurality of wells step includes contacting a first surface including the plurality of wells with a suspension comprising a plurality of cells; waiting a predetermined period of time to allow the plurality of cells to settle into the plurality of wells; and removing excess suspension.

16. The method of claim 15, wherein the suspension has a concentration of cells of between 1000 cell/mL and 500,000 cells/mL.

17. The method of claim 14, wherein the optically interrogating step includes performing fluorescence spectroscopy, fluorescence microscopy, Raman spectroscopy, Stimulated Raman Imaging, absorbance microscopy, surface plasmon resonance, infrared imaging, near-field imaging, or a combination thereof.

18. The method of claim 14, the method further comprising registering a location of the plurality of cells within the plurality of wells based on the optically interrogating step.

19. The method of claim 14, the method further comprising accounting for reflections.

20. The method of claim 14, the method further comprising introducing a product of the matrix assisted laser desorption ionizing to a mass spectrometer.

* * * * *